(12) United States Patent
Kriesel et al.

(10) Patent No.: US 8,197,445 B2
(45) Date of Patent: Jun. 12, 2012

(54) PAIN MANAGEMENT DISPENSER

(75) Inventors: Marshall S. Kriesel, St. Paul, MN (US); Joshua W. Kriesel, San Francisco, CA (US); Donald B. Bivin, Oakland, CA (US); Alan D. Langerud, Plymouth, MN (US)

(73) Assignee: BioQuiddity, Inc., San Francisco, CA (US)

( * ) Notice: Subject to any disclaimer, the term of this patent is extended or adjusted under 35 U.S.C. 154(b) by 301 days.

(21) Appl. No.: 12/455,618

(22) Filed: Jun. 3, 2009

(65) Prior Publication Data
US 2010/0312187 A1    Dec. 9, 2010

(51) Int. Cl.
*A61M 37/00* (2006.01)
(52) U.S. Cl. ....................................... 604/132
(58) Field of Classification Search .................. 604/132
See application file for complete search history.

(56) References Cited

U.S. PATENT DOCUMENTS

| | | | |
|---|---|---|---|
| 2,236,084 A | 3/1941 | Brown | |
| 3,884,228 A | 5/1975 | Hahn | |
| 5,009,251 A | 4/1991 | Pike et al. | |
| 5,380,287 A | 1/1995 | Kikuchi et al. | |
| 5,632,315 A | 5/1997 | Rose | |
| 6,056,716 A * | 5/2000 | D'Antonio et al. | 604/68 |
| 6,236,624 B1 | 5/2001 | Kriesel et al. | |
| 6,355,019 B1 | 3/2002 | Kriesel et al. | |
| 6,416,495 B1 | 7/2002 | Kriesel et al. | |
| 2005/0277882 A1 * | 12/2005 | Kriesel | 604/131 |

* cited by examiner

*Primary Examiner* — Nicholas Lucchesi
*Assistant Examiner* — Jason Flick
(74) *Attorney, Agent, or Firm* — James E. Brunton

(57) ABSTRACT

A dispensing device for dispensing pain management medicaments to a patient comprising first and second threadably interconnectable sub-assemblies. The first of these sub-assemblies houses a novel collapsible fluid reservoir defining component while the second comprises a fluid delivery and control assembly that includes a novel flow control means that functions to control the flow of medicinal fluid from the fluid reservoir of the collapsible reservoir defining component toward the patient via a plurality of fluid flow control passageways.

27 Claims, 23 Drawing Sheets

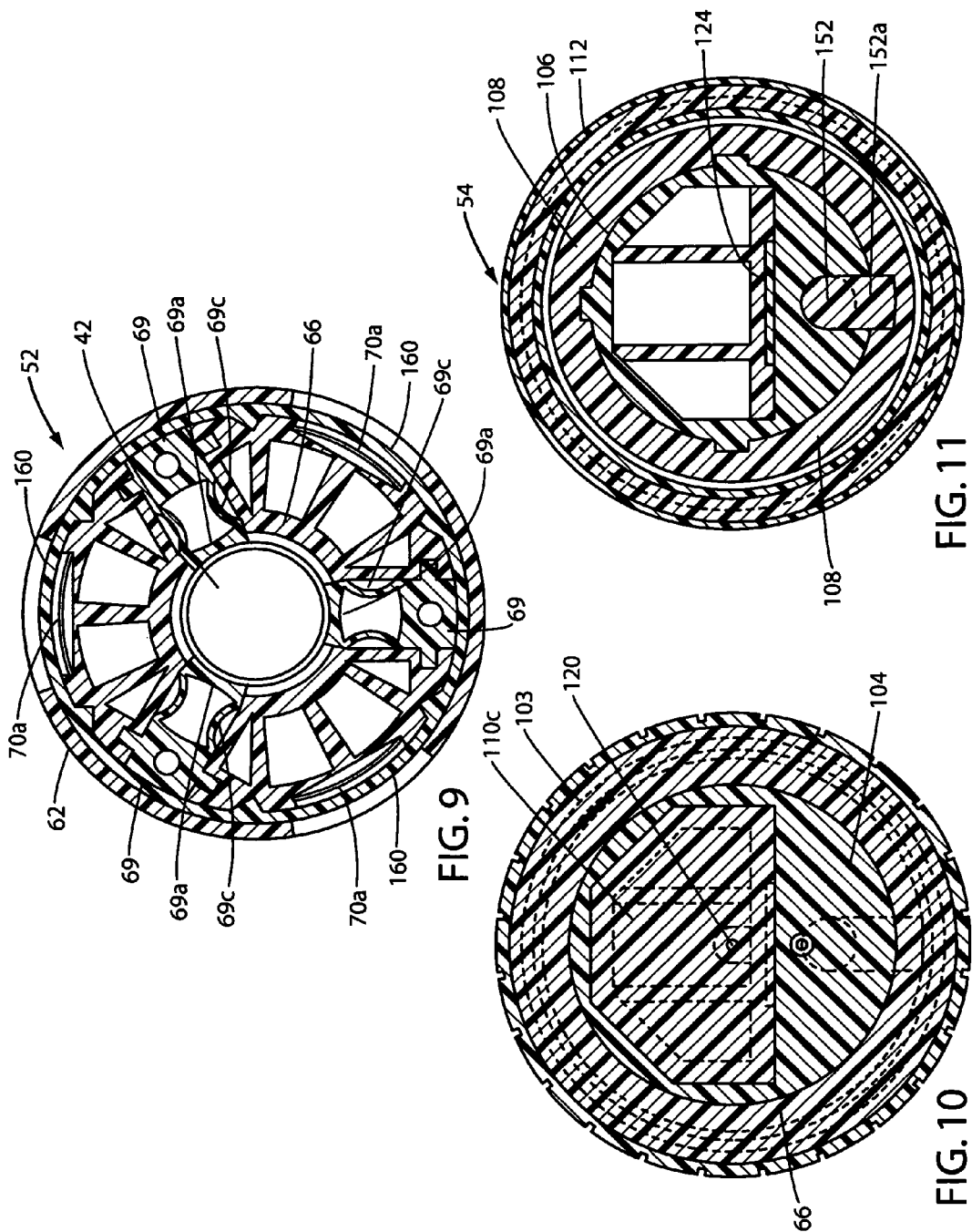

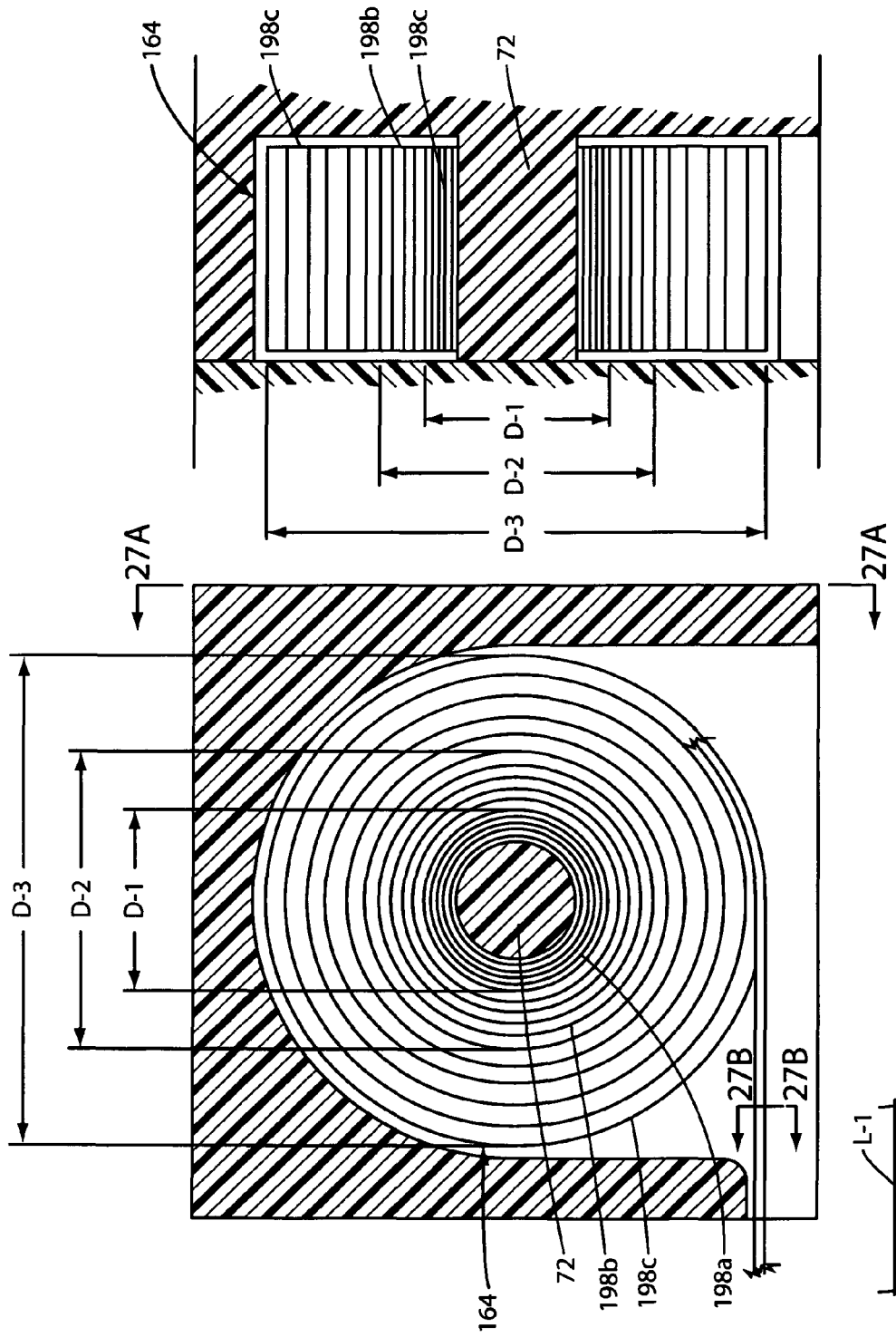
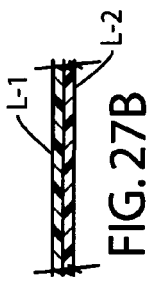
FIG. 27A
FIG. 27
FIG. 27B

PAIN MANAGEMENT DISPENSER

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

The present invention relates generally to fluid dispensing devices. More particularly, the invention concerns a novel pain management dispenser for dispensing medicinal fluids, such as Bupivacane to ambulatory patients that uniquely comprises a flow rate control system that regulates the pressure of medicaments flowing to the patient.

2. Description of Related Art Including Information Disclosed Under 37 CFR 1.97 and 1.98

A number of different types of medicament dispensers for dispensing medicaments to ambulatory patients have been suggested in the past. Many of the devices seek either to improve or to replace the traditional gravity flow and hypodermic syringe methods which have been the standard for delivery of liquid medicaments for many years.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to one of the present applicants, namely U.S. Pat. No. 5,743,879, discloses an injectable medicament dispenser for use in controllably dispensing fluid medicaments such as insulin, anti-infectives, analgesics, oncolylotics, cardiac drugs, bio-pharmaceuticals, and the like from a pre-filled container at a uniform rate. The dispenser, which is quite dissimilar in construction and operation from that of the present invention, includes a stored energy source in the form of a compressively deformable, polymeric, elastomeric member that provides the force necessary to controllably discharge the medicament from a pre-filled container which is housed within the body of the device. After having been deformed, the polymeric, elastomeric member will return to its starting configuration in a highly predictable manner.

A more recent fluid dispensing apparatus invented by one of the named inventors of the present application is disclosed in U.S. Pat. No. 7,220,245. This apparatus comprises a compact fluid dispenser for use in controllably dispensing fluid medicaments, such as, antibiotics, oncolylotics, hormones, steroids, blood clotting agents, analgesics, and like medicinal agents from prefilled containers at a uniform rate. The dispenser uniquely includes a stored energy source that is provided in the form of a substantially constant-force, compressible-expandable wave spring that provides the force necessary to continuously and uniformly expel fluid from the device reservoir. The device further includes a fluid flow control assembly that precisely controls the flow of medicament solution to the patient.

BRIEF SUMMARY OF THE INVENTION

By way of brief summary, one form of the dispensing device of the present invention for dispensing pain management medicaments to a patient comprises first and second threadably interconnectable sub-assemblies. The first of these sub-assemblies houses a fluid reservoir defining component while the second comprises a fluid delivery and control assembly that includes a novel flow control means that functions to control the flow of medicinal fluid from the fluid reservoir of the first sub-assembly toward the patient via a plurality of fluid flow control passageways.

By way of brief background of the fluid dispensing system of the present invention has been created to provide safe and efficacious drug and fluid delivery in hospitals, surgery centers, home care, austere environments, and other alternate sites of care. The fluid delivery systems are uniquely configured for use at the point-of-care and will allow drug or fluid infusion to be initiated during virtually any phase of care, in any healthcare setting, and continue uninterrupted, while en-route to other medical facilities or during rehabilitation.

Additionally, the self-contained and therapy-specific nature of the fluid delivery systems functions to reduce the probability of costly and potentially life-threatening medication errors. In this regard, the fluid delivery systems of the invention are consistent with the growing trend of unit-dosing, where clinicians, pharmacists and regulators agree that a "unit of use" is the preferred form of containerization for liquid and solid medicines to be administered in hospital, home, or alternate site settings. Unit-dose packaging is preferred because of its inherent ability to reduce the possibility of medication error, while promoting the use of bar coding at the point of care. The unit-dose drug delivery dispensers of the present invention are also equally well suited for use in the inpatient hospital environment, where surgeries that are more complex, require longer recovery times, or cannot be sustained in a surgicenter setting are still performed.

With the forgoing in mind, it is an object of the present invention to provide a novel to provide safe and efficacious drug and fluid delivery system that can be efficiently used in hospitals, surgery centers, home care, austere environments, and other alternate sites of care.

Another object of the invention is to provide a drug and fluid delivery system of the aforementioned character that is specifically configured for use at the point-of-care and one which will allow drug or fluid infusion to be initiated during virtually any phase of care, in any healthcare setting, and continue uninterrupted, while en-route to other medical facilities or during rehabilitation.

Another object of the invention is to provide a fluid dispensing system that can be used for controllably dispensing at a uniform rate a wide variety of fluid medicaments, such as Bupivacane, Ropivaciane, Propofol and like medicinal.

Another object of the invention is to provide a pain management dispensing apparatus of the aforementioned character, dispenser of simple construction and one that can be used in the home care environment with a minimum amount of training.

Another object of the invention is to allow infusion therapy to be initiated quickly at the point of care without the assistance of a medical professional.

Another object of the invention is to provide a novel dispensing apparatus in which a stored energy source is provided in the form of a compressible, expandable or retractable member of novel construction that provides the force necessary to continuously and uniformly expel fluid from the device reservoir.

Another object of the invention is to provide a dispenser of the character described in the preceding paragraphs in which the stored energy source is provided in the form of a variable force spring that comprises a tightly coiled wound band of pre-hardened, perforated spring steel or stainless steel strip with built-in curvature so that each turn of the strip wraps tightly on its inner neighbor. When the strip is extended (deflected), the inherent stress resists the loading force the same as a common extension spring but at a variable rate.

Another object of the invention is to provide a dispenser of the class described which includes a fluid flow control assembly that precisely controls the flow of the medicament solution to the patient.

Another object of the invention is to provide a fluid dispensing apparatus that enables precise variable flow rate selection.

Another object of the invention is to provide a fluid dispensing apparatus of the character described in the preceding paragraphs that embodies an integrally formed, aseptically filled, unitary semi-rigid collapsible container that includes a fluid reservoir that contains the beneficial agents to be delivered to the patient.

Another object of the invention is to provide a fluid dispensing apparatus of the class described which is compact and lightweight, is easy for ambulatory patients to use and is extremely reliable in operation.

Another object of the invention is to provide a fluid dispensing apparatus that is easy and inexpensive to manufacture in large quantities.

BRIEF DESCRIPTION OF SEVERAL VIEWS OF THE DRAWINGS

FIG. 9 is a cross-sectional view taken along lines 9-9 of FIG. 2.

FIG. 10 is a cross-sectional view taken along lines 10-10 of FIG. 2.

FIG. 11 is a cross-sectional view taken along lines 11-11 of FIG. 2.

FIG. 27 is an enlarged cross-sectional view of one form of the variable force spring assembly usable with the embodiment of the invention shown in FIGS. 25 and 26.

FIG. 27A is a cross-sectional view taken along lines 27A-27A of FIG. 27.

FIG. 27B is a cross-sectional view taken along lines 27B-27B of FIG. 27.

DETAILED DESCRIPTION OF THE INVENTION

Definitions

Figure 1:
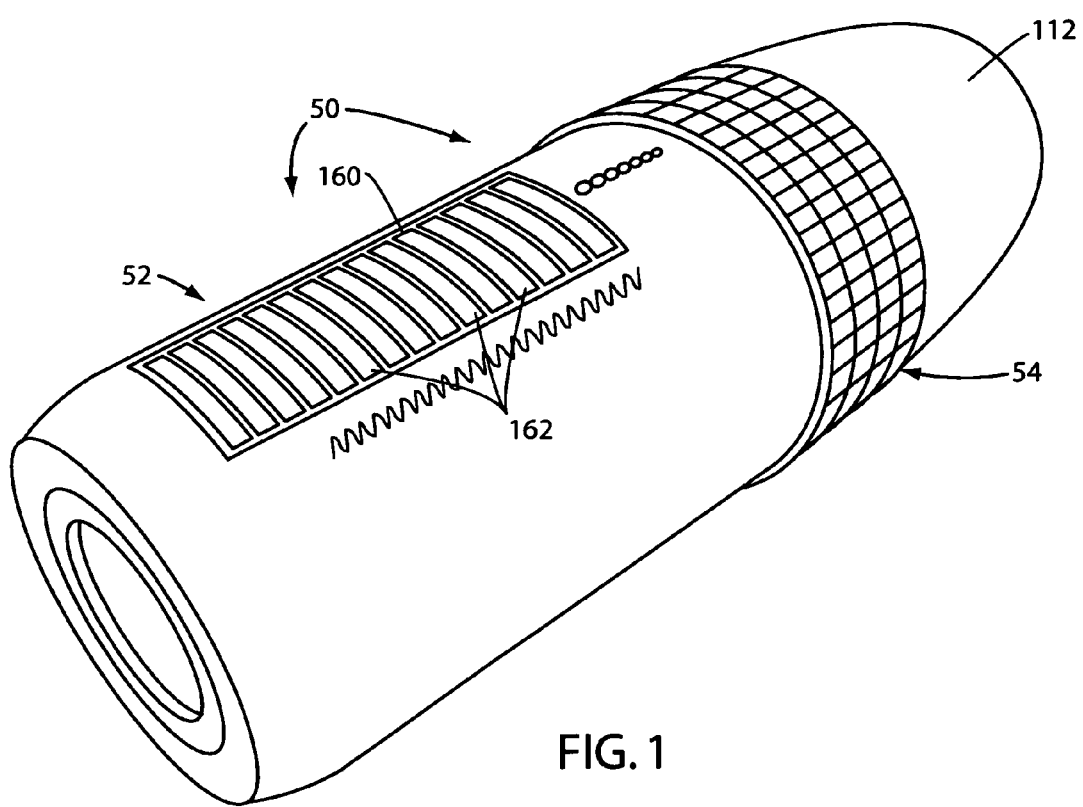
FIG. 1 is a generally perspective rear view of one form of the pain management dispensing system of the present invention.

As used herein the following terms mean:
Unitary Container:
A closed container formed from a single component.
Continuous/Uninterrupted Wall:
A wall having no break in uniformity or continuity.
Hermetically Sealed Container:
A container that is designed and intended to be secure against the entry of microorganisms and to maintain the safety and quality of its contents after pressurizing.
Aseptic Processing:
The term 'aseptic processing' as it is applied in the pharmaceutical industry refers to the assembly of sterilized components and product in a specialized clean environment.
Sterile Product:
A sterile product is one that is free from all living organisms, whether in a vegetative or spore state.
Blow-Fill-Seal Process:
The concept of aseptic blow-fill-seal (BFS) is that a container is formed, filled, and sealed as a unitary container in a continuous manner without human intervention in a sterile enclosed area inside a machine. The process is multi-stepped; pharmaceutical grade resin is extruded into a tube, which is then formed into a container. A mandrel is inserted into the newly formed container and filled. The container is then sealed, all inside a sterile shrouded chamber. The product is then discharged to a non-sterile area for packaging and distribution.
Collapsible Container:
A dispensing apparatus in which one or more walls of the container are made of a material which will deform (collapse) when pressure is applied thereto; or a dispensing apparatus having a collapsible or telescoping wall structure.
Constant Force Spring:
Constant force springs are a special variety of extension spring. They are tightly coiled wound bands of pre-hardened spring steel or stainless steel strip with built-in curvature so that each turn of the strip wraps tightly on its inner neighbor. When the strip is extended (deflected), the inherent stress resists the loading force; the same as a common extension spring but at a nearly constant (zero) rate. The constant-force spring is well suited to long extensions with no load build-up. In use, the spring is usually mounted with the ID tightly wrapped on a drum and the free end attached to the loading force. Considerable flexibility is possible with constant-force springs because the load capacity can be multiplied by using two or more strips in tandem, or back-to-back. Constant force springs are available in a wide variety of sizes.
Modified Constant Force Spring (Variable Force Spring):
The modified constant force spring or variable force spring of the present invention comprises a spring of highly novel configuration that includes an elongated, pre-stressed strip of spring material that may be metal, a polymer, a plastic, or a composite material with built-in curvature so that, like the conventional constant force spring, each turn of the strip wraps tightly on its inner neighbor. Uniquely, in one form of the invention the elongated pre-stressed strip of spring material exhibits a cross-sectional mass that varies along said length. This variation in cross-sectional mass along the length of the spring can be achieved in various ways, as for example, by varying the width of the pre-stressed strip along its length and by providing spaced-apart apertures in the pre-stressed strip along its length. In another form of the invention, the pre-stressed strip of spring material is coiled about the spring drum to predetermined varying degrees of tightness. Accordingly, similar to the variable force spring having a variation in cross-sectional mass along the length of the spring, a variation of coil tightness can produce highly specific and desirable linear and non-linear force-distention curves.

Figure 2:
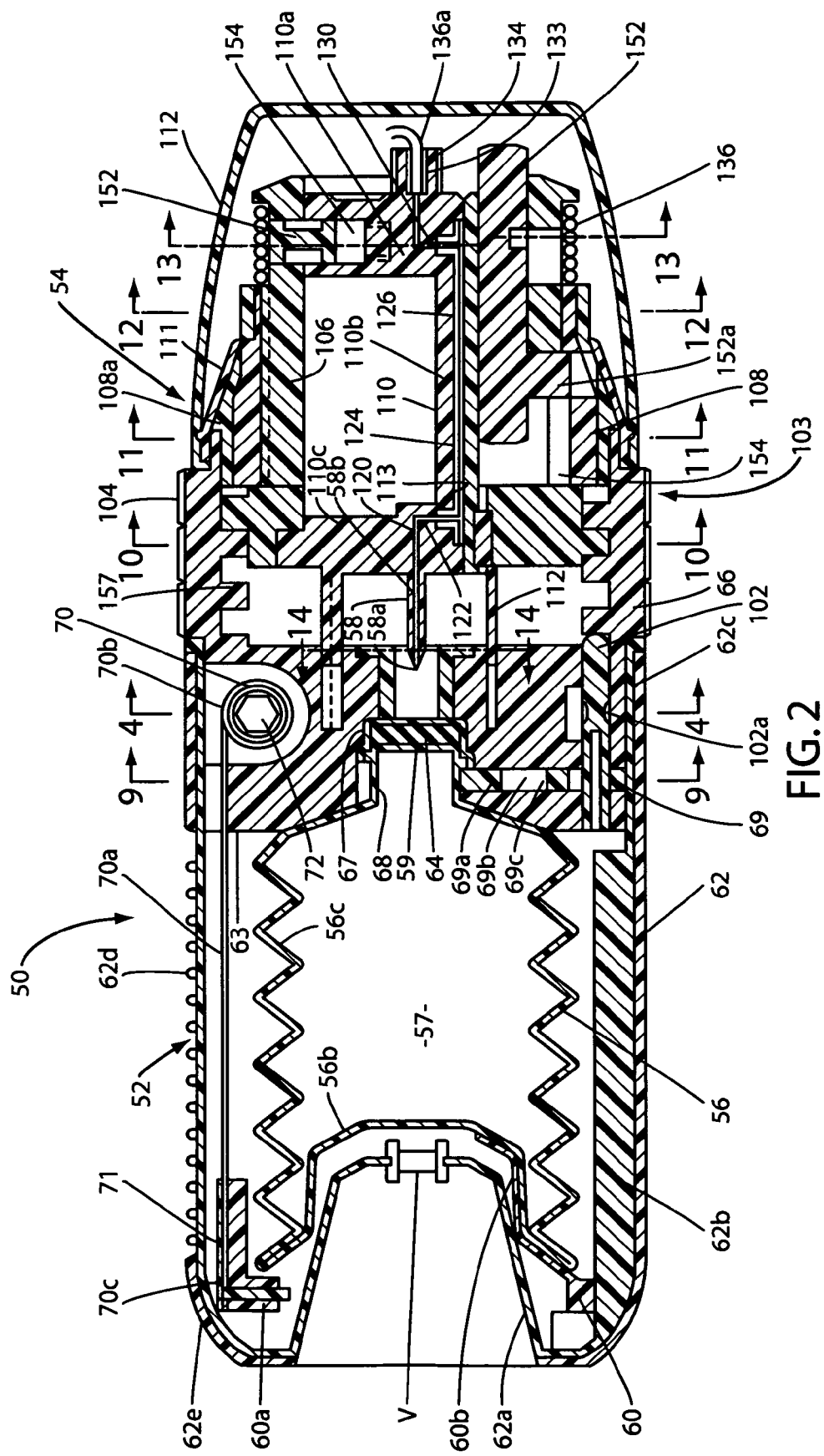
FIG. 2 is a longitudinal cross-sectional view of the fluid dispensing system shown in FIG. 1 of the drawings.

Referring to the drawings and particularly to FIGS. 1 and 2, one form of the fluid dispensing apparatus of the present invention for dispensing medicaments is there shown. The dispensing apparatus, which is generally designated in FIG. 1 by the numeral 50, comprises two threadably interconnectable assemblies 52 and 54. As best seen in FIG. 2 of the drawings, assembly 52 comprises a fluid reservoir assembly that houses a fluid reservoir defining component here shown as a hermetically sealed collapsible container 56. Assembly 54, on the other hand comprises a fluid delivery and control assembly that includes a penetrating member 58 and a novel fluid flow control means that functions to control the flow of medicinal fluid toward the patient upon relative rotation of the first and second assemblies.

Figure 20:
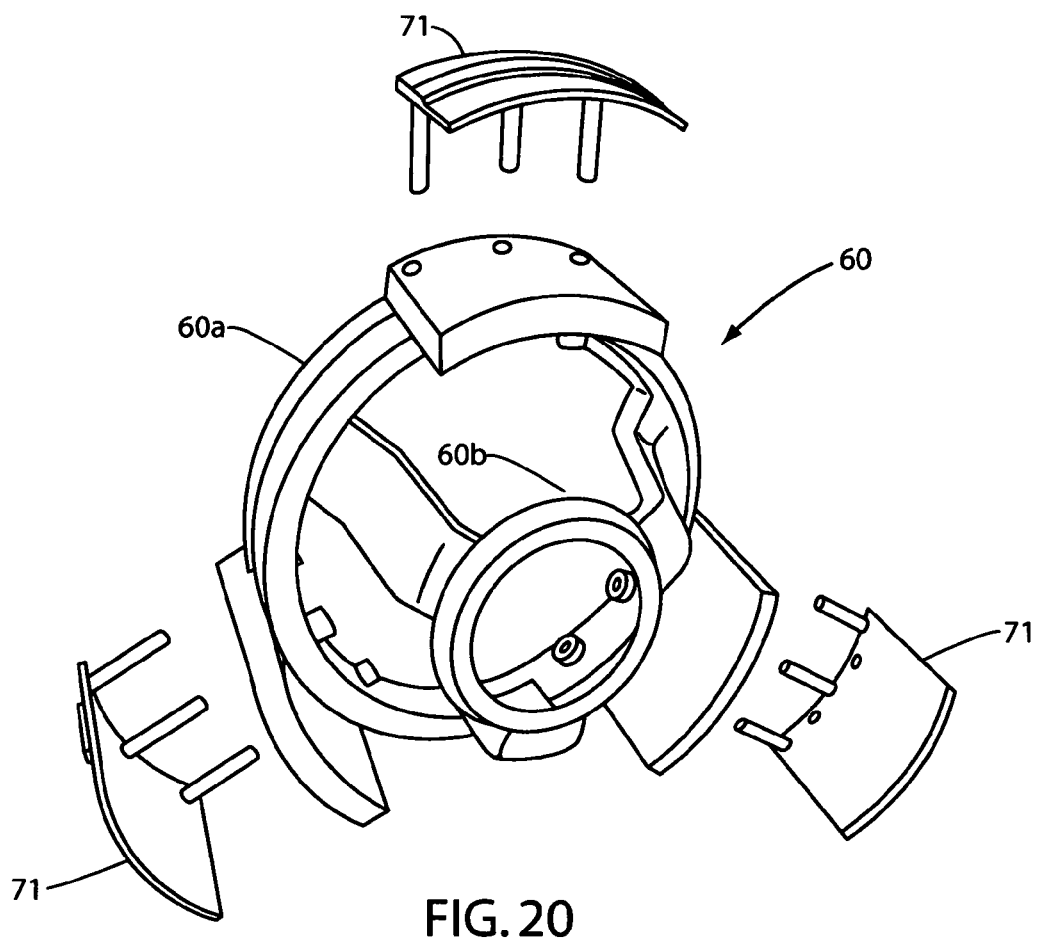
FIG. 20 is a generally perspective, enlarged exploded view showing the details of construction of the carriage assembly of the first subassembly of the apparatus of the invention.

Considering first the fluid reservoir assembly 52, in addition to the reservoir defining component 56, this assembly includes a carriage 60 and a stored energy means that is operably associated with the carriage for, upon relative rotation of the first and second assemblies, moving the carriage between a first retracted position shown in FIG. 2 and a second advanced, fluid delivery position. As best seen by referring to FIGS. 2 and 20, carriage 60 includes a base 60*a*, an outwardly extending reservoir receiving body 60*b* and a plurality of spring securement subassemblies 71 that are connected to base 60*a*. The details of construction of spring securement subassemblies 71 will be described in the paragraphs which follow.

The reservoir defining component 56, the carriage 60 and a novel stored energy means are all housed within a generally cylindrically shaped reservoir housing 62 that includes a base 62*a*, an outer wall 62*b* having a reduced diameter forward portion 62*c*. An elastomer shell 62*d* covers outer wall 62*b* and a portion of base 62*a* is covered with an elastomer coating 62*e*. Base 62*a* is provided with a gas vent "V" for venting to atmosphere any gases trapped within the fluid reservoir assembly. Connected to forward portion 62*c* is a main body portion that includes an internally threaded advancement ring 66, the function of which will presently be described.

Figure 22:
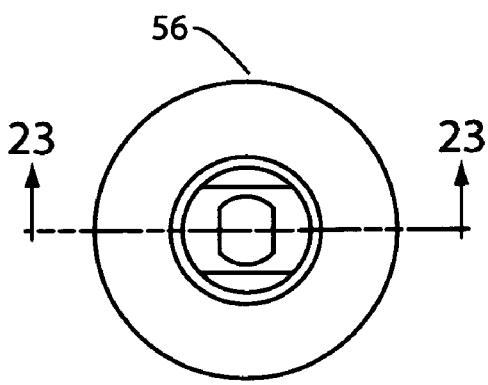
FIG. 22 is an enlarged top plan view of one form of the hermetically sealed collapsible container of the invention.
Figure 23:
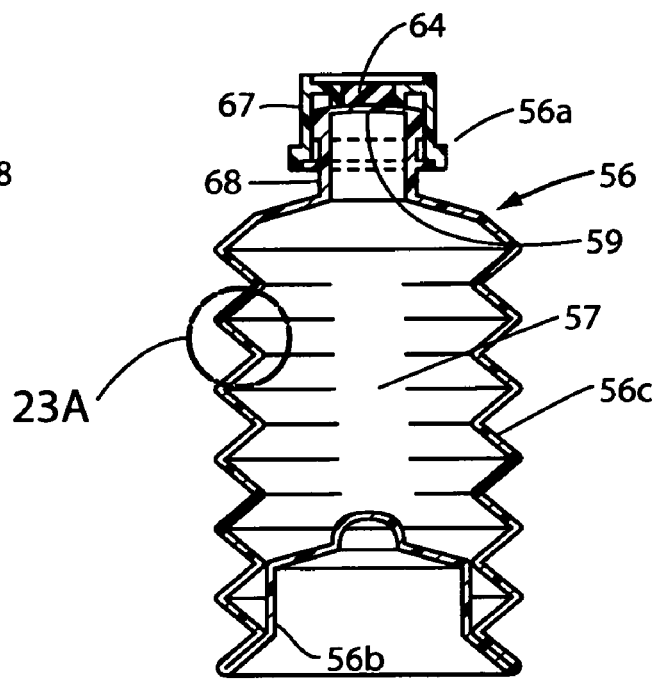
FIG. 23 is a cross-sectional view taken along lines 23-23 of FIG. 22.

As best seen in FIGS. 2, 22 and 23, reservoir defining component 56 here comprises an integrally formed, hermetically sealed container that includes a fluid medicament reservoir 57. Reservoir defining component 56 includes a front portion 56*a*, a rear, inwardly extending, ullage defining wall portion 56*b* and a collapsible accordion-like, continuous, uninterrupted side wall 56*c* that interconnects the front and rear portion of the container. In a manner presently to be described, fluid medicament reservoir 57 is accessible via a penetrating member 58 which forms the inlet to the fluid delivery and control assembly 54. More particularly, penetrating member 58 is adapted to pierce a top, or closure wall 59 of the reservoir defining component 56 as well as a pierceable septum 64 (FIGS. 2, 23 and 24) which is secured in position over closure wall 59 by means of a closure cap 67 which is affixed to the neck portion 68 of the reservoir defining component.

Figure 24:
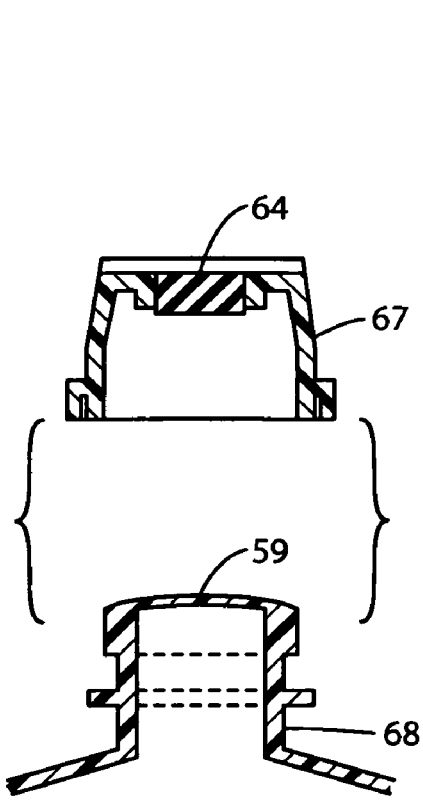
FIG. 24 is an enlarged, fragmentary exploded view of the upper portion of the collapsible container shown in FIG. 23.
Figure 23A:
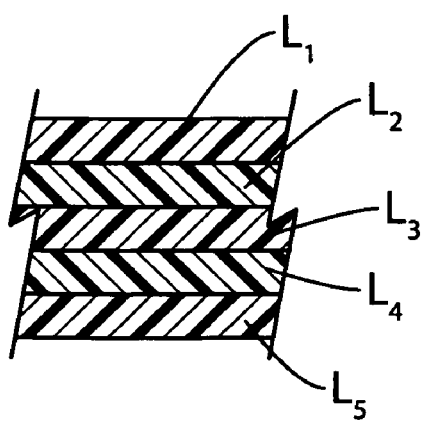
FIG. 23A is a greatly enlarged cross-sectional view of the area designated as "23A" in FIG. 23.

The reservoir defining component 56 is of a laminate construction (see FIG. 23A) and is uniquely co-extruded by an aseptic blow fill technique. As best seen in FIGS. 23 and 24, the reservoir portion of the container is sealed by the thin closure or top wall 59. The continuous top, bottom and accordion sidewalls 59, 56b and 56c cooperate to define sealed medicament reservoir 57. Prior to heat sterilization of the container, the piercable septum 64 is positioned over the closure wall and the closure cap 67 is positioned over the piercable septum and is secured to the neck portion 68 by any suitable means such as adhesive bonding, sonic welding or heat welding (see FIG. 24). As depicted in FIG. 23, the wall of the reservoir defining component 56 comprises five laminates, L-1, L-2, L-3, L-4 and L-5.

By way of background, co-extrusion in the blow-fill-seal process is typically used in the prior art to package liquids that are either oxygen or moisture sensitive. Further, oxygen sensitive products, as well as compounds that need a longer shelf life, are frequently packaged using co-extruded plastic. Blow-Fill-Seal is a preferred drug packaging modality because polypropylene (PP) and polyethylene are typically used. Compared to a traditional flexible solution bag made from PVC, a PP or PE, the blow-fill-seal container is much less permeable.

With suitable resins, co-extruded plastic blow-fill-seal containers can readily be constructed to prevent water vapor loss out of container, and ingress of oxygen into the container contents. The typical co-extruded material is a five layer system that exhibits substantially the same thickness as a comparable container constructed from a single layer resin material. That is, each layer is ⅕ of the equivalent container that is homogeneous (non-laminate). However, it should be recognized that, at a minimum a three layer system is required to suit the purposes of the present invention, while a system having up to about 10 layers would be feasible for certain applications.

In a typical five layer co-extruded blow-fill-seal container, the laminate material may comprise an inert internal polyolefin, such as PP. The barrier material in the center of the five layer laminate may be selected to exhibit gas or water barrier properties, or both. The barrier material is affixed to the inert hydrophobic plastic layer (e.g. PP) via a binder layer.

Although a variety of plastic resins may be used for the co-extrusion of blow-fill-seal containers, polyolefins (e.g. PP of LDPE) are desirable to be in contact with the parenteral solution, as this material is inert and hydrophobic.

It is well know in the food packaging industry that Ethylene-Vinyl Alcohol Copolymer (EVOH) is an excellent gas barrier. Additionally, a variety of nylon based materials (also referred to as polyamides (PA)) can act as strong vapor barriers. Those skilled in the art will also recognize cyclic polyolefin copolymers (COP) for their effectives as water barriers, and therefore there use in co-extruded blow-fill-seal containers.

Other suitable barrier materials may included, but are not limited to, polyvinyl chloride, oriented polyvinyl chloride (OPVC), biaxially oriented PET, silica-deposited resins, sequentially biaxially oriented polyvinyl alcohol, biaxially oriented polyester, vinylidene chloride (or copolymers of vinylidene chloride and methyl methacrylate), polyacrylonitrile (PAN), oriented polyethylene terephthalate (OPET), polystyrene (PS), ethylene methyl acrylate copolymer (EMA), and other polymer resins known to those skilled in the art which are generally termed "high gas barrier polymers" HBP. Additionally, those skilled in the art will recognize multi-lamellar barrier materials, such as those based on the blends of high-density polyethylene (HDPE) and co-polyester (PETG) prepared via melt extrusion, and poly(ethylene-co-acrylic acid) (EAA) as a compatibilizer incorporated into the blends, as possible barrier materials as well.

A variety of binder materials may be used to "tie" the dissimilar polyolefin and the barrier materials together. These include, but are not limited to agents of the formula AMXP in which AM is a backbone copolymer prepared by copolymerizing propylene with α-olefins and where X is selected from among citraconic anhydride, fumaric acid, mesaconic acid, the anhydride of 3-allylsuccinic acid and maleic anhydride, and P is a polyamide oligomer prepared from caprolactam, 11-aminoundecanoic acid or dodecalactam; ethylene vinyl acetate copolymer (EVA); a coextrusion binder comprising a metallocene polyethylene (A1), a cografting monomer said cografting monomer being an unsaturated carboxylic acid grafting monomer or functional acid derivative thereof, and an ethylene homopolymer; an ethylene copolymer wherein the comonomer is (a) an alpha-olefin, (b) an ester of an unsaturated carboxylic acid or (c) a vinyl ester of a saturated carboxylic acid; and a hydrocarbon elastomeric copolymer; and Celanex (polybutylene terephthalate (PBT) copolymer binder).

Although the most common coextrusion systems seem to be a 5 layer laminate, a variety of different "size" laminate materials would be workable in BioQ dispensers and fit the spirit of the expanded invention. At a minimum, a three layer sandwich would be required (i.e. inert polyolefin, binder and barrier) would be required. At a maximum, many repeated layers that comprise both oxygen and moisture barriers would be feasible.

The container is held in position within housing 62 by means of a container locking assembly generally designated in FIG. 2 by the numeral 69. Locking assembly 69 includes a locking member 69a which is telescopically movable within a transverse chamber 69b. Locking assembly 69 also includes a coil spring 69c that urges member 69a into the locking, or container capture position shown in FIG. 2 of the drawings.

The previously mentioned stored energy means that is operably associated with the carriage 60 for moving the carriage between a first retracted position and a second advanced, fluid delivery position here comprises a plurality of uniquely modified constant force springs that are identified in the drawings by the numeral 70. By way of background, conventional constant force springs are a special variety of extension spring. They comprise tightly coiled wound bands of pre-hardened spring steel or stainless steel strip with built-in curvature so that each turn of the strip wraps tightly on its inner neighbor. When the strip is extended (uncoiled), the inherent stress resists the loading force the same as a common extension spring but at a nearly constant (zero) rate.

The stored energy means of one form of the present invention comprises modified constant-force springs in which the stainless steel strip, or band, portion of the spring 70a has been uniquely modified to exhibit a cross-sectional mass that varies along the length of the band. This variation in cross-sectional mass along the length of the spring can be achieved in various ways, as for example, by providing spaced-apart apertures in the pre-stressed strip along its length in the manner illustrated in FIGS. 14 and 17.

The variation in cross-sectional mass along the length of the spring can also be achieved by changing the thickness of the band and by varying the width of the pre-stressed band along its length. In this regard, increasing the mass of material in the "force generating region" of the spring will increase the force provided by the spring. Conversely, decreasing the mass of material in the "force generating region" will result in a reduction of the force generated by the spring.

Figure 14:
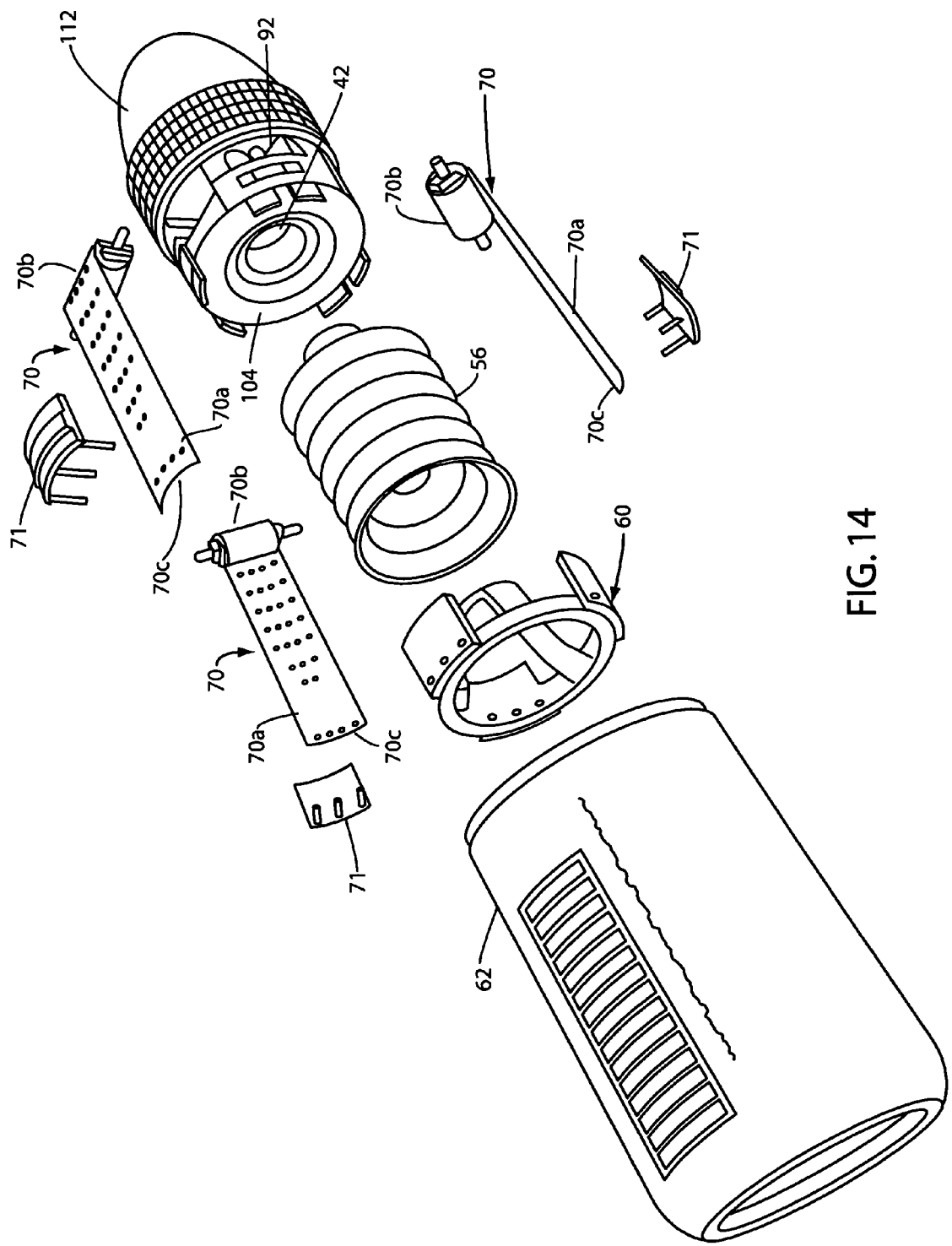
FIG. 14 is a generally perspective, exploded view showing the details of construction of the first subassembly of the apparatus of the invention.
Figure 17:
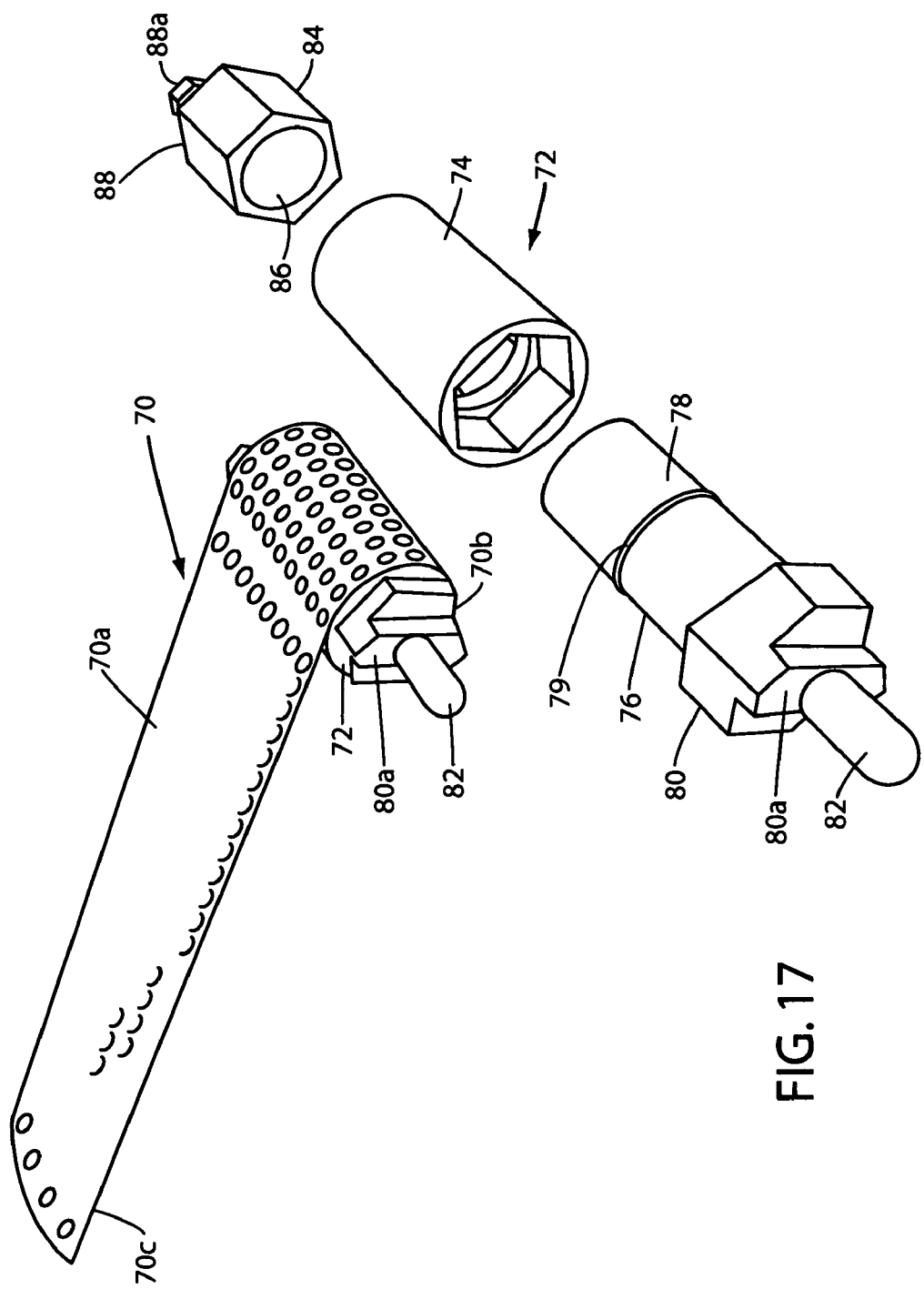
FIG. 17 is a generally perspective, enlarged exploded, view showing the details of construction of one of the variable force spring assemblies of the apparatus of the invention.

As best seen in FIGS. 2, 14 and 17, springs 70 are mounted with one end 70b tightly wrapped on a drum assembly 72 that is housed within main body portion 63 that forms a part of assembly 52 and the other end 70c attached to carriage 60 by spring clamping members 71 in the manner shown in FIG. 2.

Figure 18:
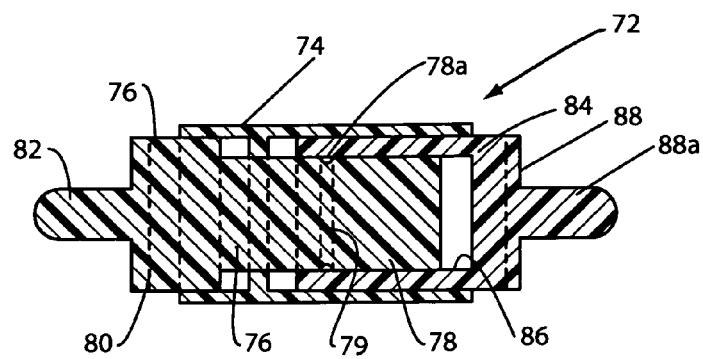
FIG. 18 is an enlarged cross-sectional view showing the details of construction of the variable force spring shaft subassembly of the variable force spring assembly depicted in FIG. 17.
Figure 19:
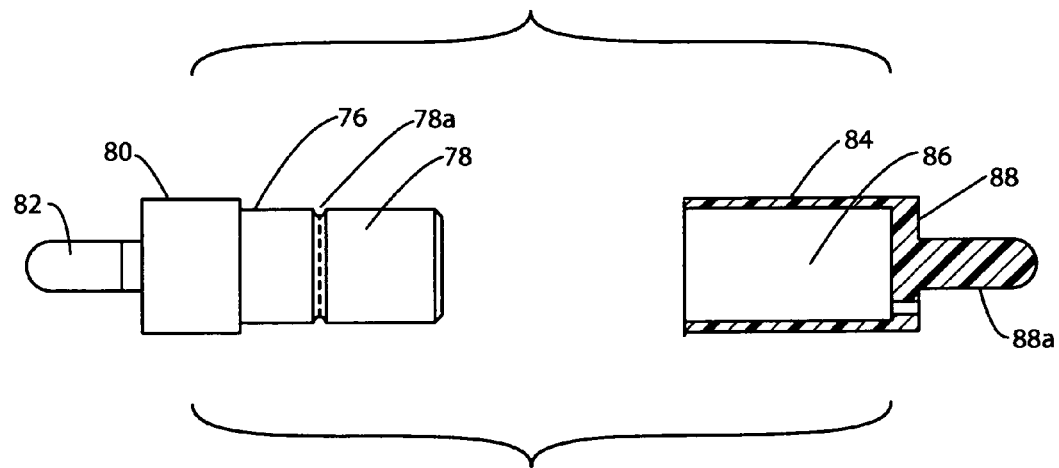
FIG. 19 is an enlarged exploded view partly in cross-section of the variable force spring shaft subassembly shown in FIG. 18.

Referring particularly to FIGS. 17, 18 and 19 of the drawings, the configuration of one of the three identical, circumferentially spaced drum assemblies 72 is there illustrated. As indicated in FIG. 18, each of the drum assembly 72 comprises a spring housing 74 about which one of the springs 70 is coiled. Received within spring housing 74 is a superior spring shaft 76 that includes a body portion 78 having an O-ring groove 78a for carrying an O-ring 79, a specially configured end portion 80, and a first actuator spring engaging protuberance 82. Also forming a part of drum assembly 72 is an inferior spring shaft 84 that includes a chamber 86 within which body portion 78 of the superior spring shaft is telescopically received for movement between a first extended position and a second retracted position. Inferior spring shaft 84 also includes an end portion 88 having a second actuator spring engaging protuberance 88a.

Figure 4:
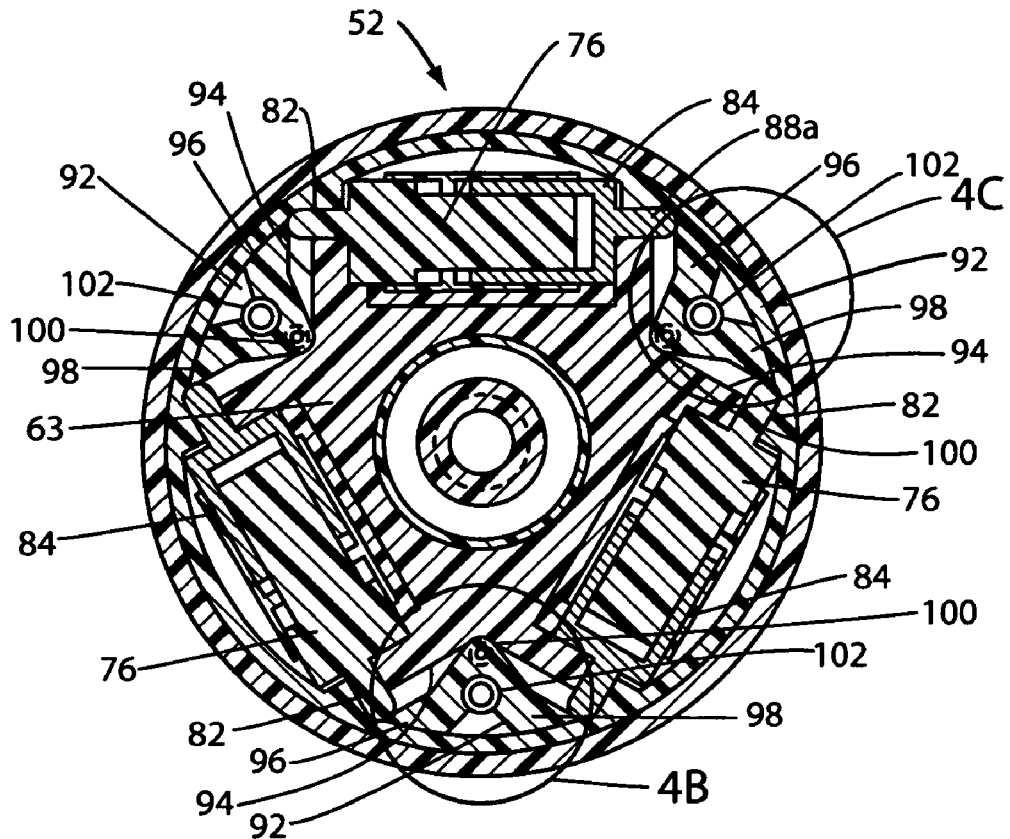
FIG. 4 is a cross-sectional view taken along lines 4-4 of FIG. 2.
Figure 4A:
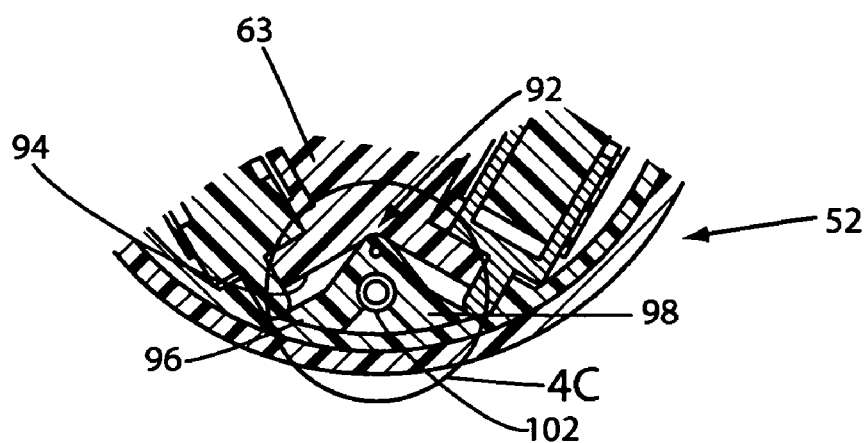
FIG. 4A is a fragmentary, cross-sectional view similar to FIG. 4, but showing the spring actuator component of the device in a spread configuration.
Figure 4B:
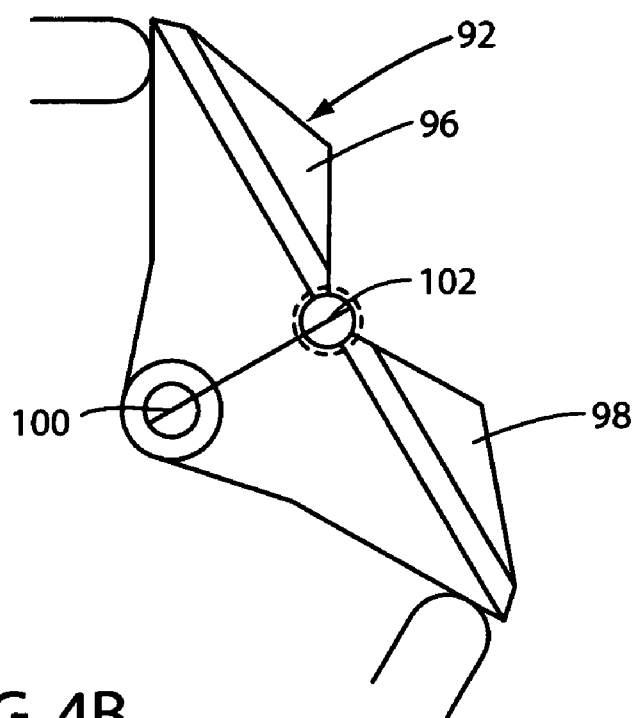
FIG. 4B is an enlarged cross-sectional view of the area designated in FIG. 4 as "4B".
Figure 4C:
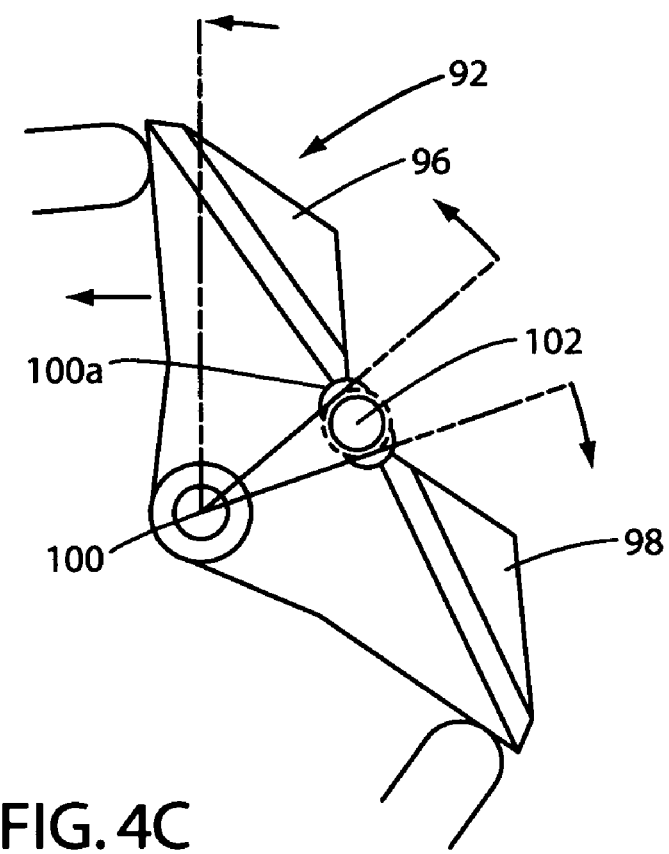
FIG. 4C is an enlarged cross-sectional view of the area designated in FIG. 4 as "4C".
Figure 4E:
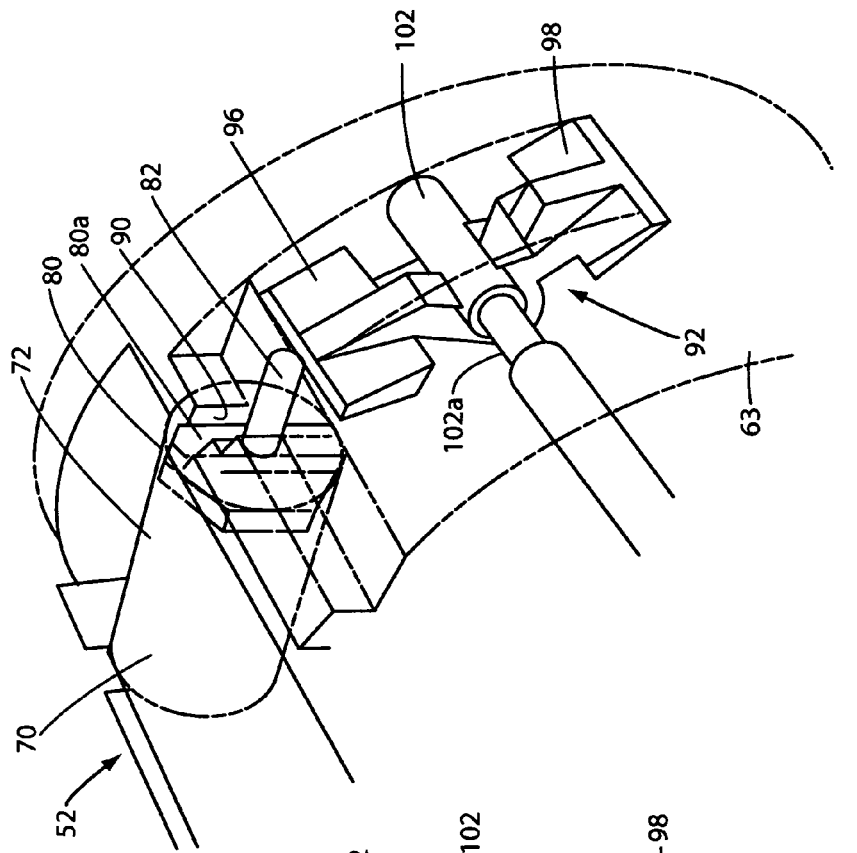
FIG. 4E is a fragmentary, generally perspective view showing one of the spring actuators of the second subassembly in a spread, or expanded configuration.
Figure 4D:
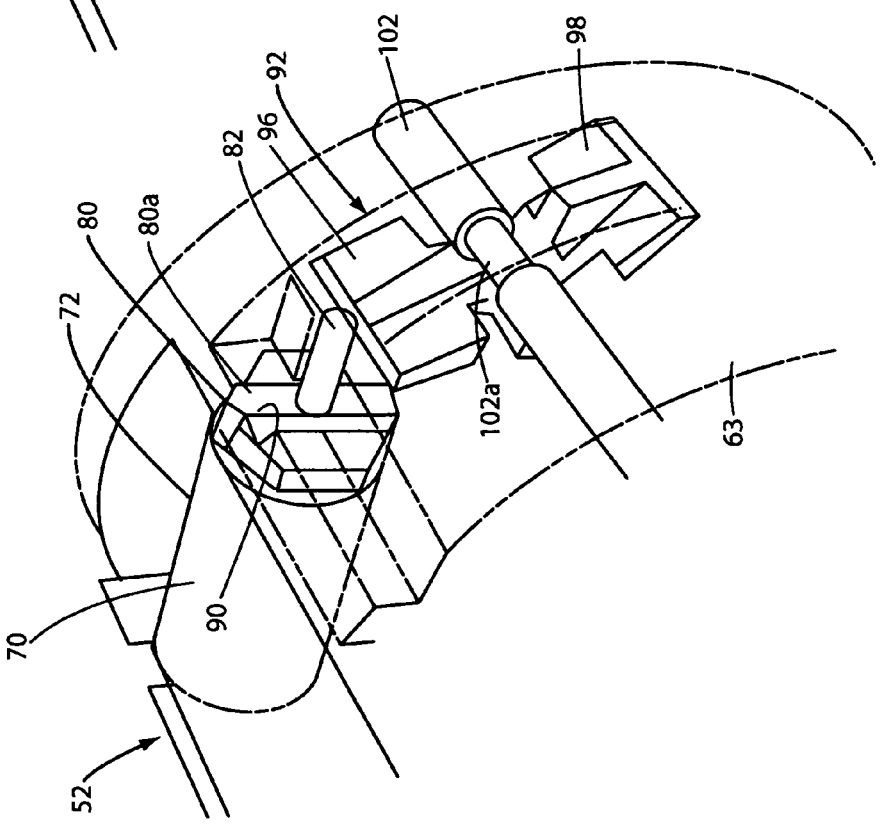
FIG. 4D is a fragmentary, generally perspective view showing one of the spring actuators of the second subassembly in a retracted configuration.
Figure 5:
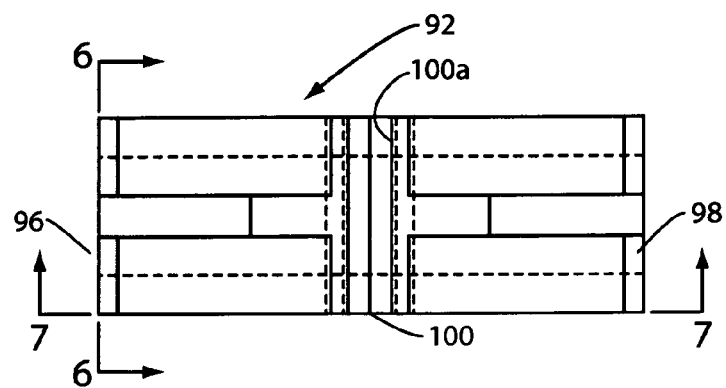
FIG. 5 is an enlarged top plan view of one of the spring actuators of the second subassembly of the apparatus of the invention.
Figure 6:
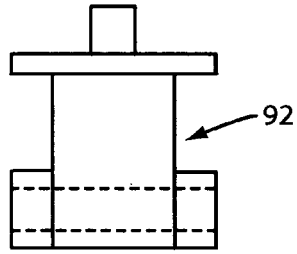
FIG. 6 is a view taken along lines 6-6 of FIG. 5.
Figure 7:
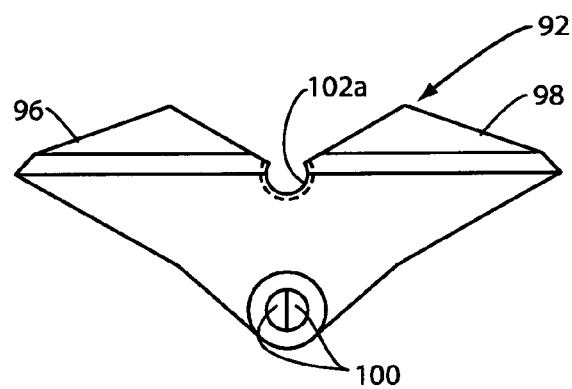
FIG. 7 is a view taken along lines 7-7 of FIG. 5.
Figure 8:
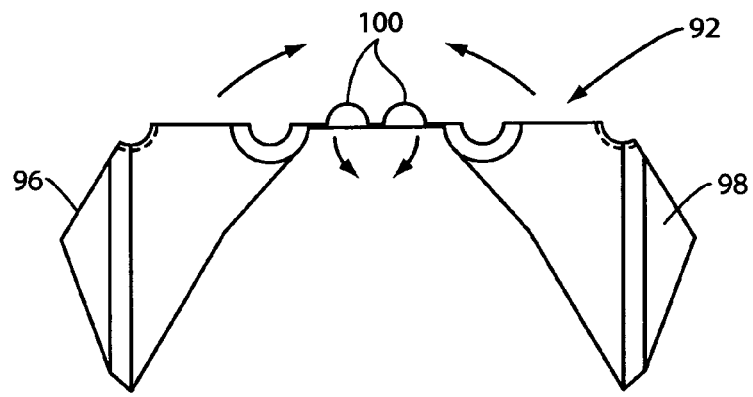
FIG. 8 is a view similar to FIG. 7, but showing the spring actuator in an open actuation position.
Figure 13:
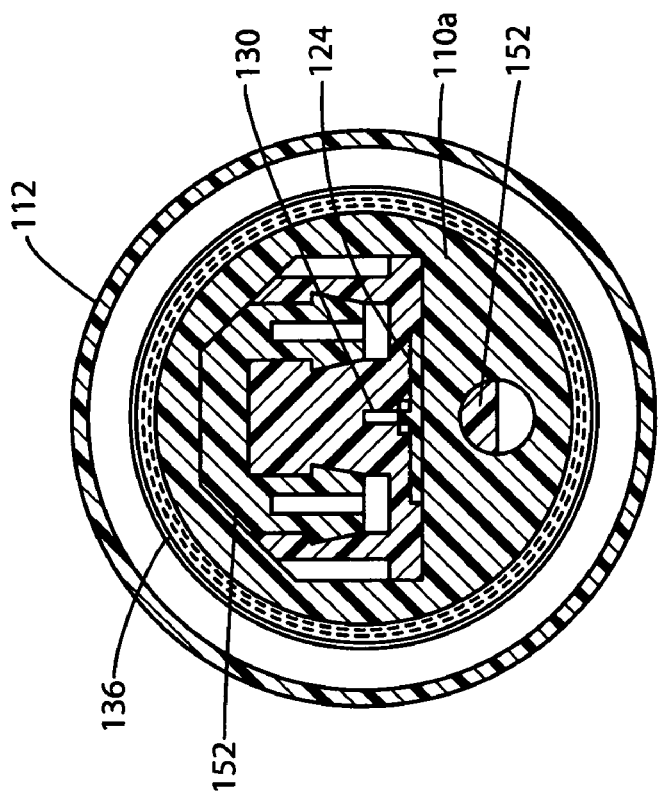
FIG. 13 is a cross-sectional view taken along lines 13-13 of FIG. 2.
Figure 12:
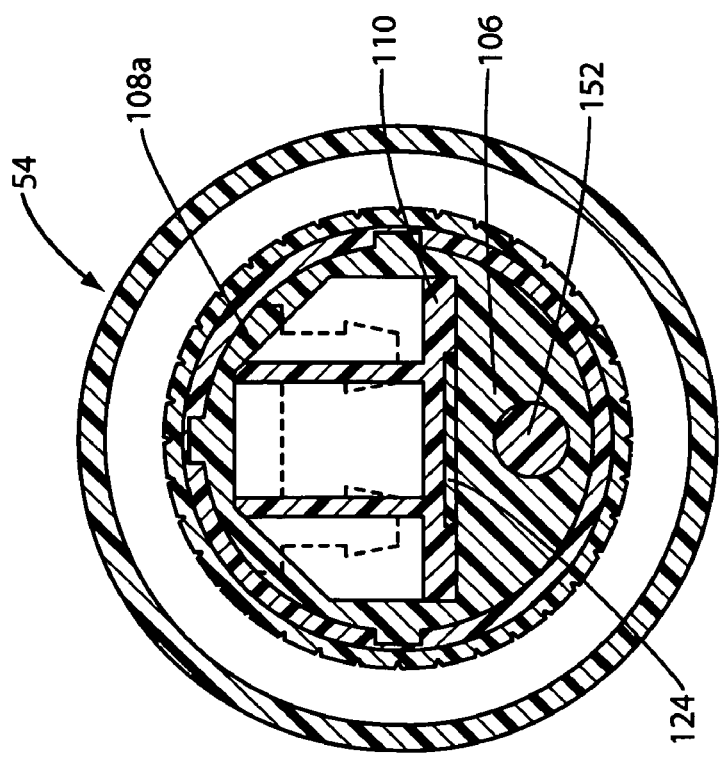
FIG. 12 is a cross-sectional view taken along lines 12-12 of FIG. 2.

Turning to FIGS. 17, 4D and 4E, it is to be noted that end portion 80 of the superior spring shaft 76 includes an outwardly extending shoulder 80a that is receivable within a locking slot 90 formed in the main body housing of assembly 52 (see FIG. 4E). So long as shoulder 80a resides within a locking slot 90, the spring 70 can not retract. However, when, in a manner presently to be described, shoulder 80a is moved out of the locking slot as a result of the action of the spring unlocking, or release means of the invention which functions to controllably release the uncoiled and locked springs, the springs will be allowed to coil about the drum assemblies 72. In the present form of the invention, this novel spring release means comprises a plurality of circumferentially spaced, uniquely configured spring actuator assemblies that function to unlock the locked springs so as to allow the springs to retract. This retraction, or recoiling, of the springs causes the carriage 60 to move forwardly of housing 52 and in so doing to controllably collapse the reservoir defining component 56.

Forming an important and novel aspect of the apparatus of the present invention is the previously mentioned spring actuator assemblies, which form a part of the spring unlocking, or release, means, are generally identified in the drawings by the numeral 92. The construction and operation of the spring actuator assemblies 92 is illustrated in FIGS. 4 through 8 of the drawings. As best seen in FIG. 4 of the drawings, the three spring actuator assemblies 92, which are carried within circumferentially spaced cavities 94 formed in the advancement ring 66, each comprise first and second actuator wings 96 and 98 that are pivotally connected to a pivot pin 100 for movement between a retracted, or closed position as shown in FIG. 4D of the drawings and an expanded or spread position as shown in FIG. 4E of the drawings. Extending through an opening 100a formed in the central portion of the actuator wings is an actuating pin 102. Each actuating pin 102 is provided with a central groove 102a (FIGS. 4D and 4E) within which the first and second actuator wings reside when the wings are in their closed position (FIG. 4D). In a manner presently to be described, during operation of the apparatus of the invention and upon relative rotation of the two threadably interconnectable assemblies 52 and 54, the actuating pins 102 will be moved rearwardly in the manner illustrated in FIG. 4E of the drawings. This movement of the actuating pins will cause the actuating wings to be moved, or cammed out of the central groove 102a, which, in turn will cause the wings to move into their expanded or spread configuration as illustrated in FIG. 4E of the drawings. As the actuating wings move into their spread configuration they will act upon the protuberances 82 and 88a of the superior and inferior spring shafts 76 and 84. More particularly, wings 96 will act upon protuberances 82 of the superior spring shaft causing the superior spring shafts 76 to telescopically move into chambers 86 of the inferior spring shafts 84. This movement of the superior spring shafts will cause outwardly extending shoulders 80a of the superior spring shafts 76 to move out of the locking slots 90 formed in the main body housing 63 of assembly 52 (see FIG. 4E) thereby permitting springs 70 to retract causing the carriage 60 to move forwardly of housing 52, which results in the collapse the reservoir defining component 56 and the delivery of fluid toward the patient.

Figure 3A:
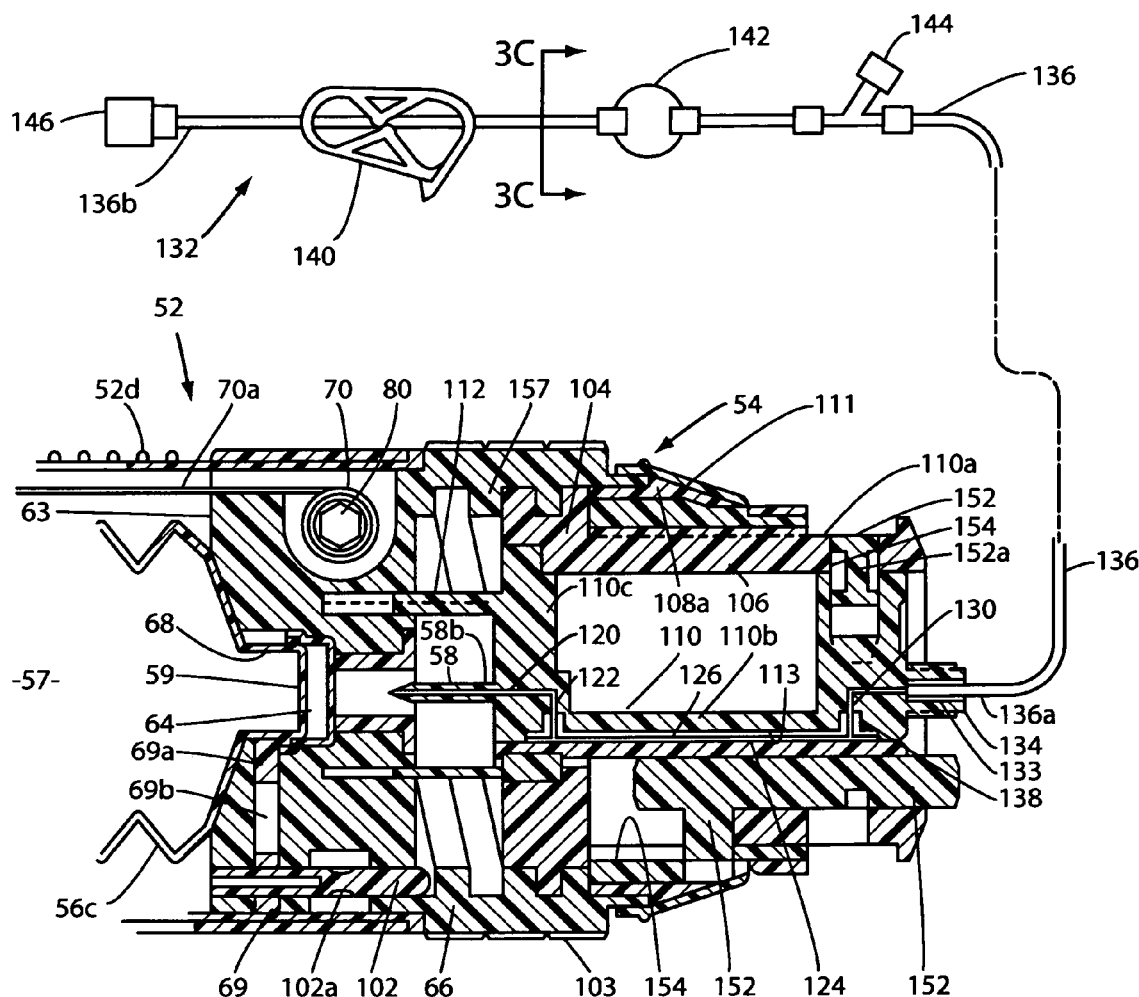
FIG. 3A is a fragmentary, longitudinal cross-sectional view similar to FIG. 2, but showing only the forward portion of the fluid dispensing system in a pre-fluid delivery condition.
Figures 3C, 3D:
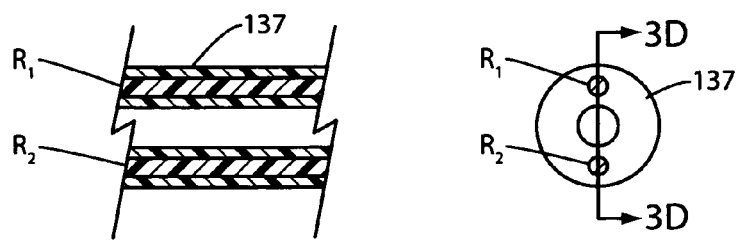
FIG. 3C is a greatly enlarged cross-sectional view taken along lines 3C-3C of FIG. 3A.
FIG. 3D is a cross-sectional view taken along lines 3D-3D of FIG. 3C.
Figure 15:
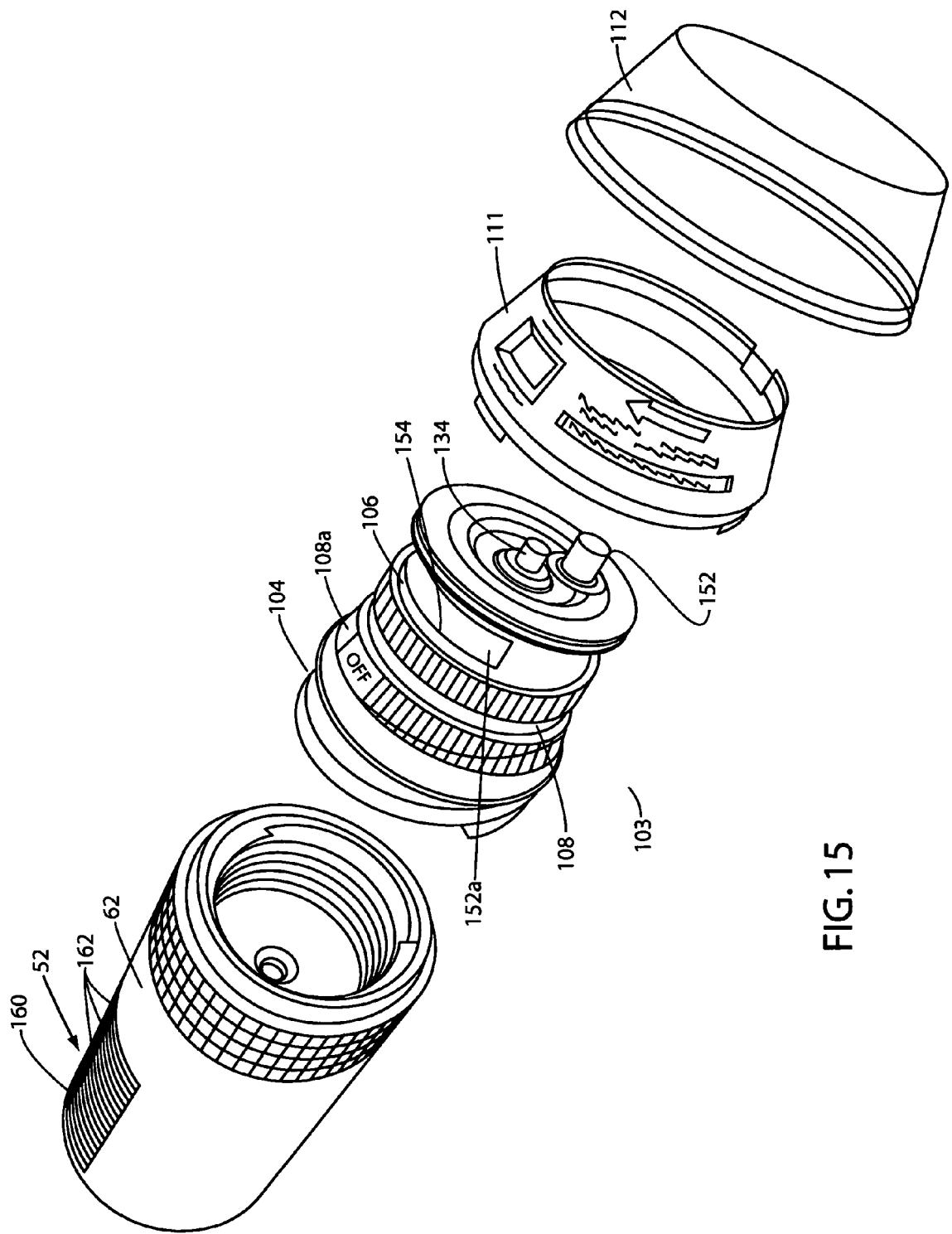
FIG. 15 is a generally perspective, exploded view showing the details of construction of the second subassembly of the apparatus of the invention.
Figure 16:
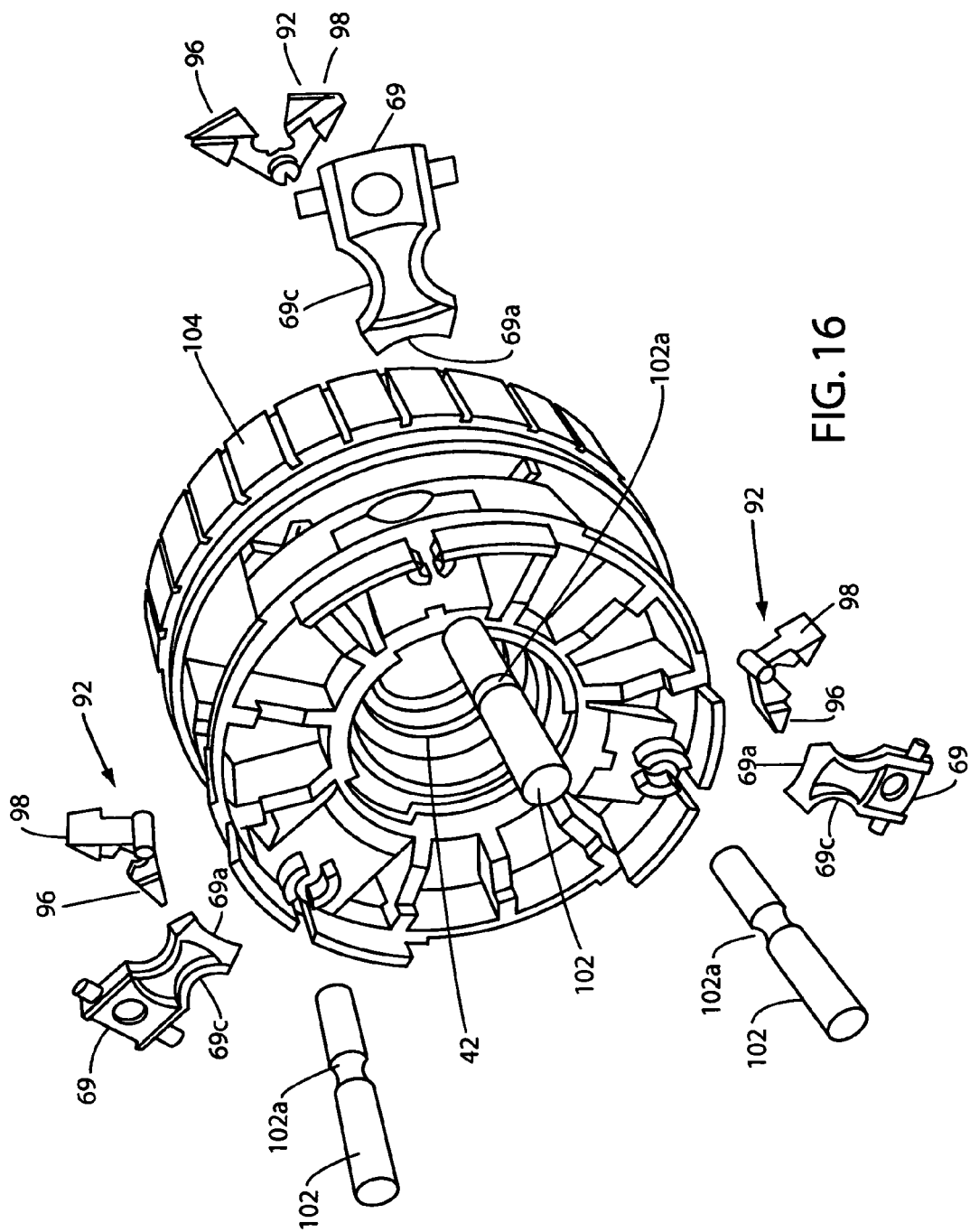
FIG. 16 is a generally perspective, enlarged exploded, view showing the details of the actuator assembly of the second subassembly of the apparatus of the invention.

Considering now the second, or control assembly 54 of the fluid dispensing apparatus, which is illustrated in FIGS. 2, 3A and 15, this assembly comprises a control housing 103, which includes a generally cylindrically shaped, internally threaded main body housing 104, a control ring 106 operably associated with the main body housing, a control ring housing 108, a control ring housing cover 108a and a rate control and piercing housing 110. Rate control and piercing housing 110 includes a forward portion 110a, an intermediate portion 110b and a rearward portion 110c. Rearward portion 110c includes a generally cylindrically shaped housing 112 that houses penetrating member 58 which has a piercing point 58a and a fluid passageway 58b which forms the inlet to the fluid delivery and control assembly 54. A rate control lens 111, the purpose of which will presently be described, circumscribes control ring housing cover 108a. Circumscribing rate control lens 111 and sealing the forward portion of the control housing 103 is a cover 112.

Intermediate portion 110b of housing 110 includes a rate control assembly chamber 113 that houses a portion of the rate control means of the present invention for controlling the rate of fluid flow from the fluid medicament reservoir 57 toward the patient. As illustrated in FIG. 2, intermediate portion 110b is also provided with a longitudinally extending fluid passageway 120 that communicates with the flow passageway 58b of the penetrating member 58a. Housing 110 is also provided with a passageway 122 that communicates with a rate control assembly 124 that is mounted within chamber 113.

Figure 21:
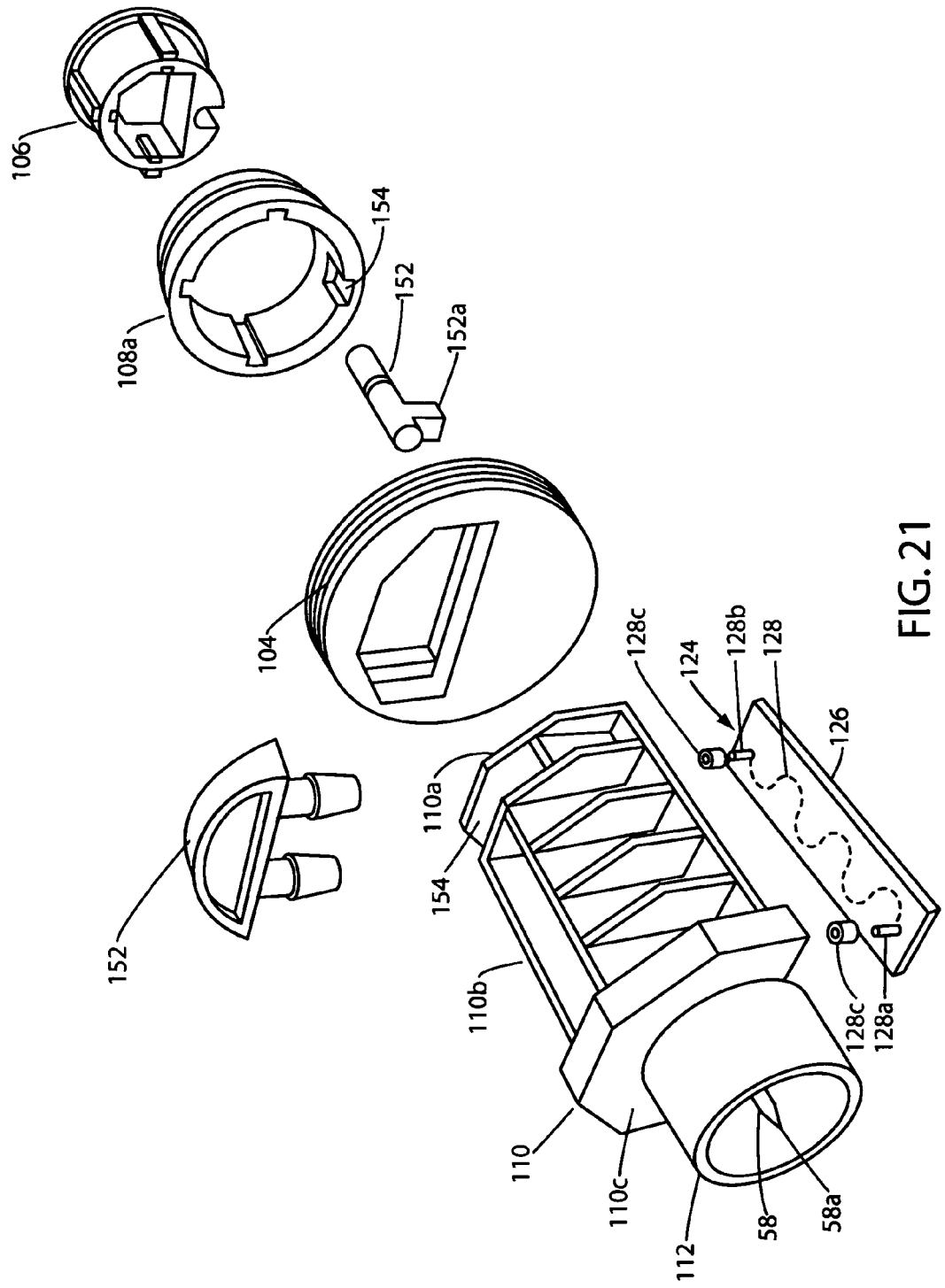
FIG. 21 is a generally perspective, enlarged exploded view showing the details of construction of the rate control assembly of the second subassembly of the apparatus of the invention.

As best seen in FIGS. 2, 3A and 21, rate control assembly 124 comprises a generally planar shaped rate control plate 126, which as shown in FIG. 21 is provided with a serpentine micro-channel 128 having an inlet 128a and an outlet 128b. Micro channel 128 which is controllably etched into rate control plate 126, communicates with passageway 130 that comprises an outlet passageway. The length, width and depth of the micro-channel determine the rate at which the fluid will flow toward outlet 130.

As shown in FIG. 3A of the drawings, an administration set 132 is sealably interconnected with an outlet port 133 formed in rate control and piercing housing 110. More particularly, the administration set 132 is connected to housing 110 by means of a connector 134 so that the proximal end 136a of the administration line 136 is in communication with an outlet fluid passageway 138 formed in housing 110. Disposed between the proximal end 136a and the distal end 136b of the administration line 137 are a conventional clamp 140, a conventional gas vent and filter 142, and a generally Y-shaped injector site, generally designated by the numeral 144. A luer connector 146 of conventional construction is provided at the distal end 136b of the administration line. Referring to FIGS.

3C and 3D it is to be noted that the administration line 137 is reinforced by a pair of elongated reinforcement filaments R-1 and R-2 that are embedded in the body 37a of the line. Filaments R-1 and R-2 can be formed from various materials including nylon, Dacron polyethylene and the like. As illustrated in FIG. 2 of the drawings, when the apparatus is in the transport and storage mode, the administration line is coiled about the control ring 106.

Figure 3B:
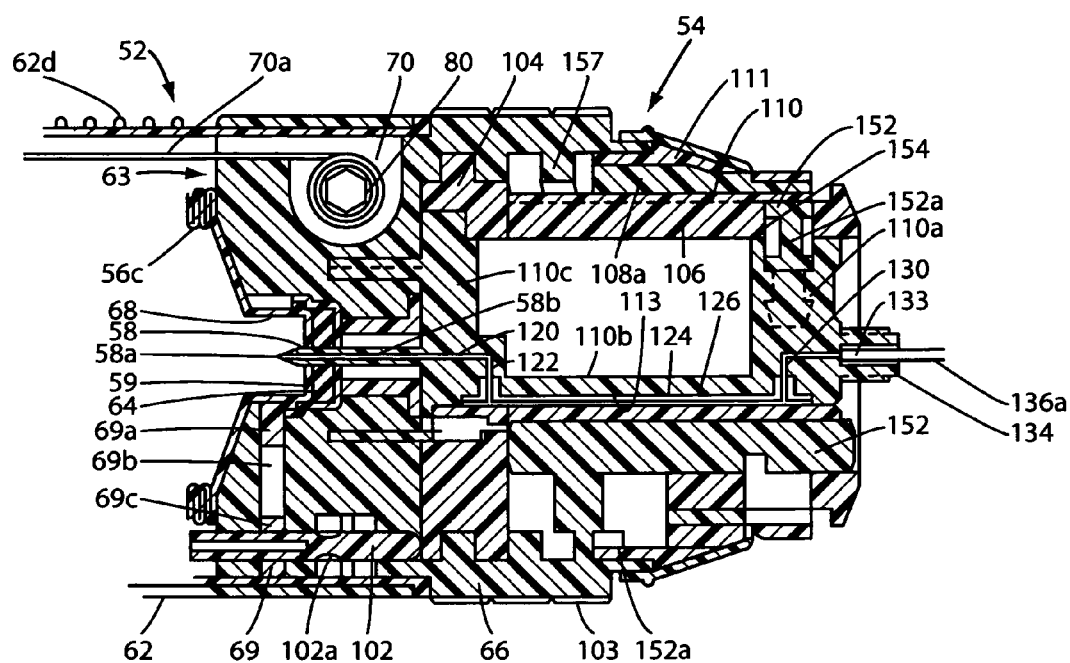
FIG. 3B is a fragmentary, longitudinal cross-sectional view similar to FIG. 3A, but showing the forward portion of the fluid dispensing system in a fluid delivery condition.

In using the apparatus of this latest form of the invention, the first step is to remove cover 112 from assembly 54. This done, the locking means of the invention is then operated. This novel locking means functions to prevent accidental relative rotation between the first and second assemblies 52 and 54. In the present form of the invention the locking means comprises a locking member 152 that is carried by assembly 54 in the manner shown in FIG. 2 of the drawings for movement between the first extended locking position shown in FIG. 3A and the second, inward release position shown in FIG. 3B. Locking member 152 is provided with a locking protuberance 152a, which when the locking member is in its first extended position, resides within a locking groove 154 formed in control ring housing, so as to prevent relative rotation between the first and second assemblies 52 and 54 (see FIG. 21). However, when the locking member is moved into its second inward release position locking protuberance 152a clears groove 154 thereby permitting relative rotation between the first and second assemblies. Upon relative rotation of the first and second assemblies, assembly 54 will advance along the threads 157 provided on first assembly 54, into the position illustrated in FIG. 3B of the drawings. As the second assembly advances, penetrating member 58 will penetrate elastomeric member, or pierceable septum 64 and closure wall 59 of the fluid reservoir defining component 56.

With communication between the fluid reservoir 57 and the internal passageway 58b of the penetrating member 58 having thusly been established, the fluid contained within the fluid reservoir will be expelled from the reservoir 57 as a result of the release of the variable force springs 70 in the manner previously described. More particularly, as the second assembly 54 advances along threads 157 into the position illustrated in FIG. 3B, portion 110c of piercing housing 110 will engage the actuating pins 102 controllably moving them rearwardly in the manner illustrated in FIG. 4E of the drawings. This movement of the actuating pins will cause the actuating wings 96 and 98 to be move into their expanded or spread configuration, as illustrated in FIG. 4E of the drawings. As the actuating wings move into their spread configuration they will act upon the protuberances 82 and 80a of the superior and inferior spring shafts 76 and 84 of drum assembly 72 causing the superior spring shafts 76 to telescopically move into chambers 86 of the inferior spring shafts 84. This movement of the superior spring shafts will cause outwardly extending shoulders 80a of the superior spring shafts 76 to move out of the locking slots 90 formed in the main body housing 63 of assembly 52 (see FIG. 4E) thereby permitting springs 70 to retract causing the carriage 60 to move forwardly of reservoir housing 52. This forward movement of the carriage 60 will cause the collapse the reservoir defining component 56, which will, in turn, cause the fluid contained within the fluid reservoir to be controllably expelled there from and to flow into internal passageway 58b of the penetrating member. In the manner previously described, the fluid will then flow toward longitudinally extending fluid passageway 120, toward passageway 122 and then toward rate control assembly 124. More particularly, the fluid will flow into the inlet 128a of the serpentine micro-channel 128, through the micro channel 128 at a controlled rate, through the outlet 128b of the micro channel, into passageway 130 and finally into the administration set for delivery to the patient at a precisely controlled rate depending upon the configuration of the micro-channel 128.

In order that the caregiver can continuously monitor the amount of fluid remaining within the fluid reservoir 57, indicator means are provided for indicating the volume of fluid contained within the reservoir. In the present form of the invention this indicator means comprises a fluid indicator window 160 provided in the housing of first assembly 52 (FIG. 1) to enable the caregiver to view the fluid reservoir 57. Indicia 162, provided on the fluid indicator window, indicates the volume of fluid contained within the reservoir.

Figure 25:
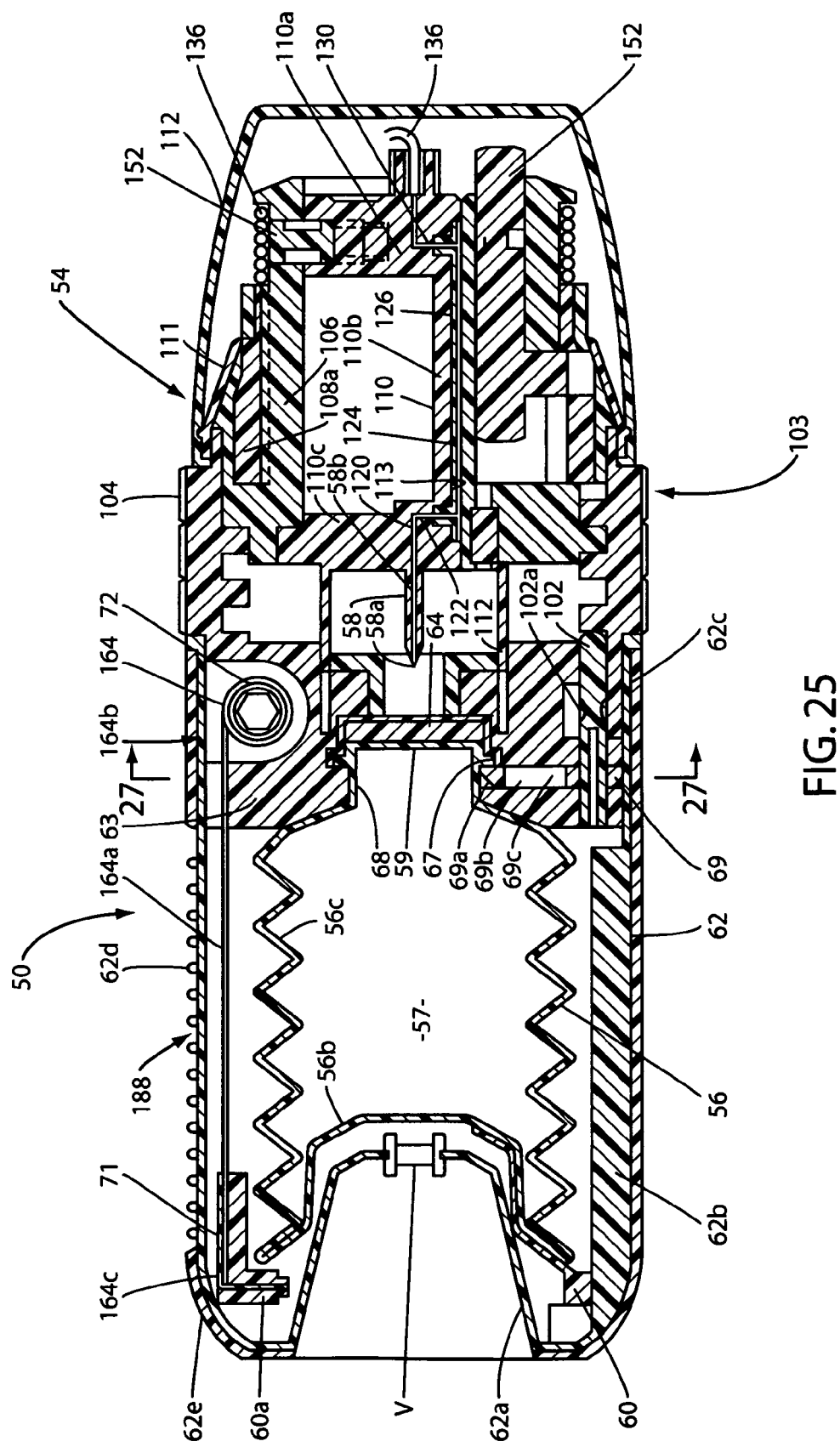
FIG. 25 is a longitudinal cross-sectional view of an alternate form of the medicament dispensing apparatus of the invention.
Figure 26:
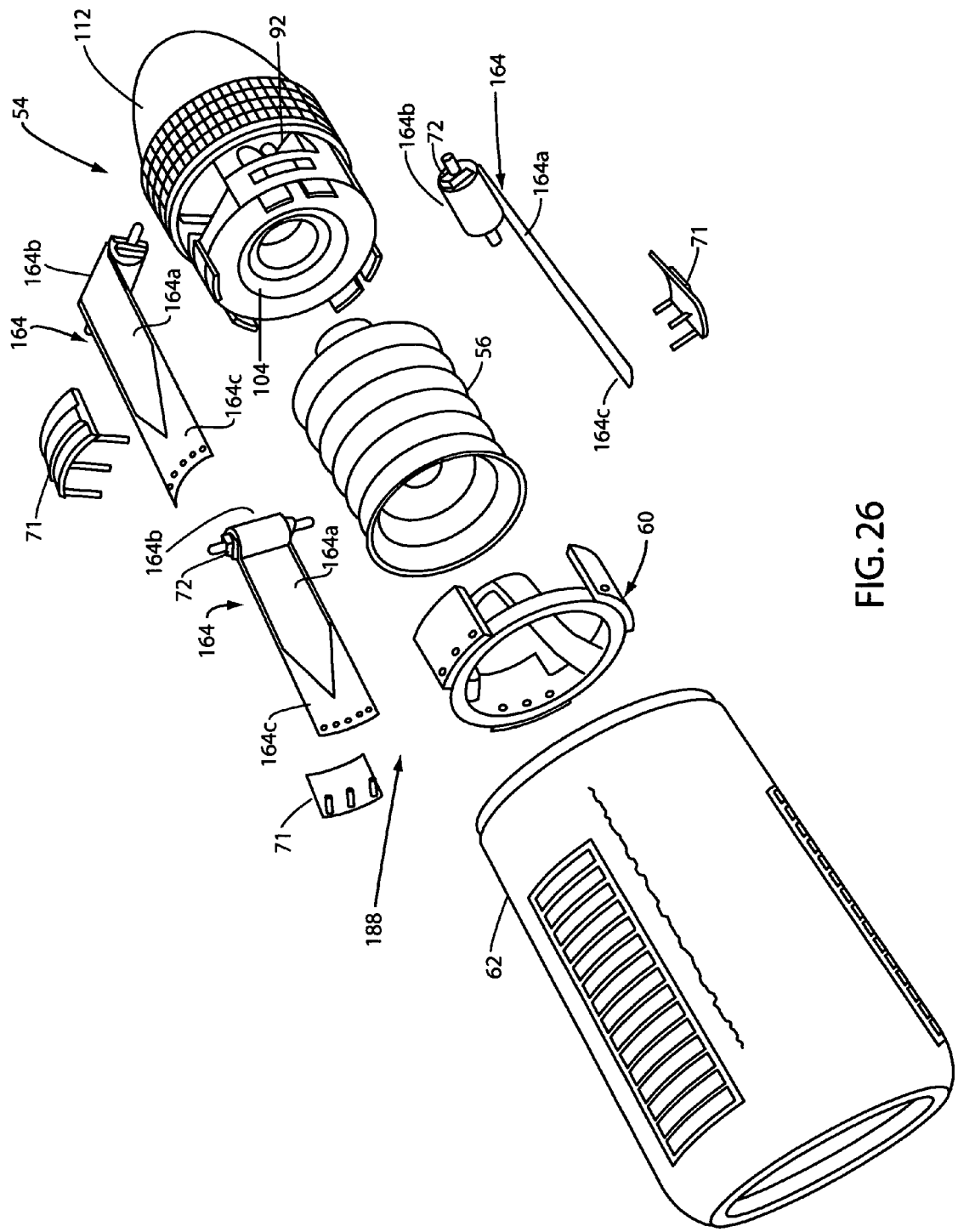
FIG. 26 is a generally perspective, exploded view of the alternate form of the apparatus shown in FIG. 25.

Turning now to FIGS. 25 and 26, an alternate form of the apparatus of the invention is there shown. This form of the apparatus is similar in many respects to the embodiment illustrated in FIGS. 1 through 24 and like numerals are used in FIGS. 25 and 26 to identify like components. The primary difference between this alternate embodiment of the invention and the earlier described embodiments resides in the differently configured stored energy means. In this latest form of the invention, the stored energy means comprises variable force springs 164 that are somewhat similar to a prior art constant force spring, but one in which the elongated band or strip portion 164a of the spring is coiled about the spring drum 72 in predetermined varying degrees of tightness (see FIGS. 27 and 27A). Accordingly, like the earlier described variable force springs in which the elongated band or strip portion of the spring has been modified to exhibit a cross-sectional mass that varies along the length of the band, springs with a variation of coil tightness can produce highly specific and desirable linear and non-linear force-distention curves to meet the fluid delivery requirements of the invention. This type of "inter-wound negative gradient" spring has no slot. In fact, the winding process is done precisely to create a "negative gradient" so that as the spring retracts, it provides a higher force. Springs with a variation of coil tightness that produce highly specific and desirable linear and non-linear force-distention curves to meet the fluid delivery requirements of the invention, are commercially available from various sources, including Vulcan Mfg. & Spring Company of Telford, Pa.

As in the earlier described embodiments of the invention, this latest apparatus comprises two threadably interconnectable assemblies, 188 and 54. Assembly 188, like the earlier described assembly 54 comprises a fluid reservoir assembly that houses a fluid reservoir defining component here shown as a hermetically sealed collapsible container 56. Assembly 54, which is substantially identical in construction and operation to that previously described, comprises a fluid delivery and control assembly that includes a penetrating member 58 and a novel fluid flow control means that functions to control the flow of medicinal fluid toward the patient.

In addition to the reservoir defining component 56, fluid reservoir assembly 188, includes a carriage 60 with which the variable force spring 164 is operably associated for moving the carriage between a first retracted position and a second advanced, fluid delivery position.

As before, variable force springs 164 are mounted with one end 164b tightly wrapped on a drum assembly 72 that is identical in construction and operation to that previously described. The other end 164c of the springs are attached to carriage 60 by spring clamping members 71 in the manner shown in FIG. 25 of the drawings.

Forming an important and novel aspect of this latest form of the apparatus of the invention is the previously mentioned spring unlocking or release means, carried by the main body portion 63 of assembly 188 and operably associated with the stored energy means for unlocking the variable force springs 164 from their locked extended position so as to permit said variable force springs to move from their locked extended position to their retracted position. As before, this spring unlocking means comprises a plurality of spring actuator assemblies that are generally identified in the drawings by the numeral 92. The construction and operation of the spring actuator assemblies 92, which is illustrated in FIGS. 4 through 8 of the drawings, is substantially identical to that previously described herein. As best seen in FIG. 4 of the drawings, the three spring actuator assemblies 92 are carried within circumferentially spaced cavities 94 formed in the main body portion 63 of assembly 188. As in the earlier described embodiment of the invention, each of the novel actuator assemblies comprises first and second actuator wings 96 and 98 that are pivotally connected to a pivot pin 100 or movement between a retracted, or closed position shown in FIG. 4D of the drawings and an expanded or spread position shown in FIG. 4E of the drawings. Extending through an opening 100a formed in the central portion of the actuator wings is an actuating pin 102. Each actuating pin 102 is provided with a central groove 102a (FIGS. 4D and 4E) within which the first and second actuator wings reside when the wings are in their closed position (FIG. 4D). In the manner previously described, during operation of the apparatus of the invention and upon relative rotation of the two threadably interconnectable assemblies 188 and 54, the actuating pins 102 will be moved rearwardly in the manner illustrated in FIG. 4E of the drawings. This movement of the actuating pins will cause the actuating wings to be moved, or cammed out of the central groove 102a, which, in turn, will cause the wings to move into their expanded or spread configuration as illustrated in FIG. 4E of the drawings. As the actuating wings move into their spread configuration they will act upon the protuberances 82 and 88a of the superior and inferior spring shafts 76 and 84. More particularly, wings 96 will act upon protuberances 82 of the superior spring shaft causing the superior spring shafts 76 to telescopically move into chambers 86 of the inferior spring shafts 84. This movement of the superior spring shafts will cause outwardly extending shoulders 88 of the superior spring shafts 76 to move out of the locking slots 90 formed in the main body housing 63 of assembly 188 thereby permitting springs 164 to retract causing the carriage 60 to move forwardly of housing 62, which results in the collapse the reservoir defining component 56 and the delivery of fluid toward the patient.

Considering once again the novel variable force spring of this latest form of the invention and referring to FIGS. 27 and 27A of the drawings, the band portion 164a of the spring is initially wound tightly about the drum 72 to produce a first segment 198a having a diameter "D-1". This done, the band portion is then coiled, or wound more loosely about the drum 72 to produce a second segment 198b having a diameter "D-2". Finally, the band portion is coiled, or wound even more loosely about the drum 584 to produce a third segment 198c having a diameter "D-3".

By coiling the springs about their respective drums with a variation of coil tightness in the manner described in the preceding paragraph and as illustrated in FIGS. 27 and 27A, springs having highly specific and desirable linear and non-linear force-distention curves can be produced which will meet the fluid delivery requirements of the invention.

Spring assemblies, such as those depicted in FIGS. 27 and 27A of the drawings, that exhibit a variation of coil tightness that produce highly specific and desirable linear and non-linear force-distention curves to meet the fluid delivery requirements of the invention, are available by custom order from various sources, including Vulcan Mfg. & Spring Company of Telford, Pa.

Turning to FIG. 27B of the drawings, it is to be observed that the band portion of spring 164 is of a laminate construction having a first laminate L-1 and a second interconnected laminate L-2. Laminates L-1 and L-2 can be of the same or dissimilar suitable spring materials depending upon the desired performance characteristics of the spring.

Figure 28:
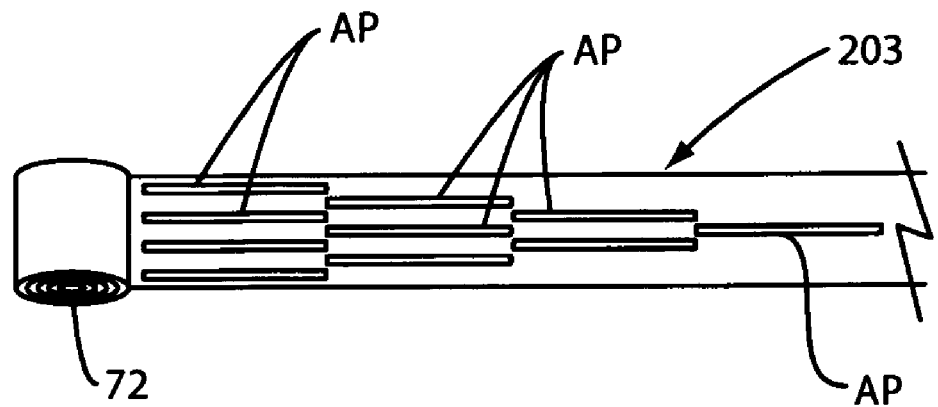
FIG. 28 is a generally perspective view of an alternate form of variable force spring usable with the apparatus illustrated in FIGS. 25 and 26.
Figure 28A:
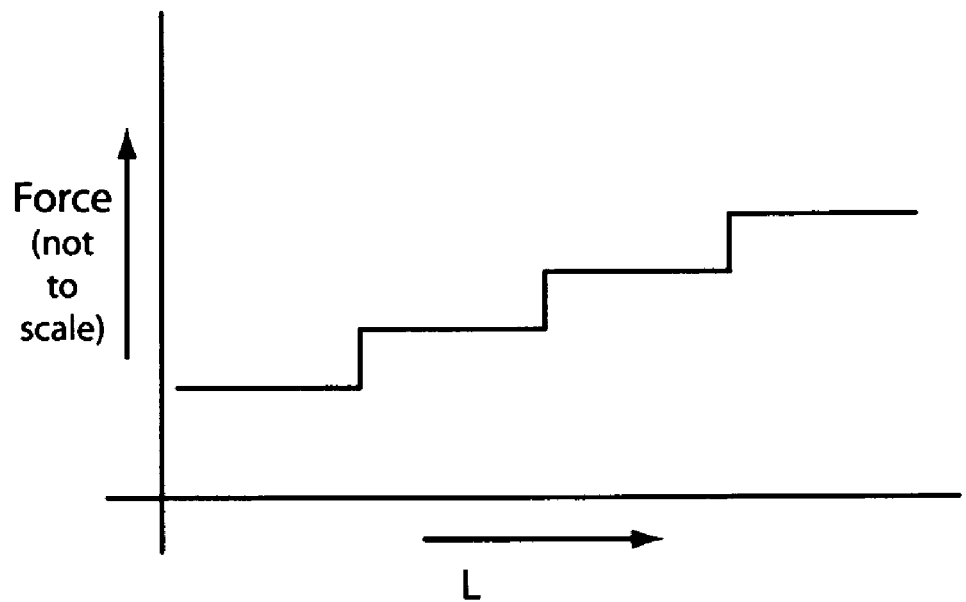
FIG. 28A is a generally graphical view plotting the force produced by the alternate form of variable force spring shown in FIG. 27 along the length of the spring.
Figure 28B:
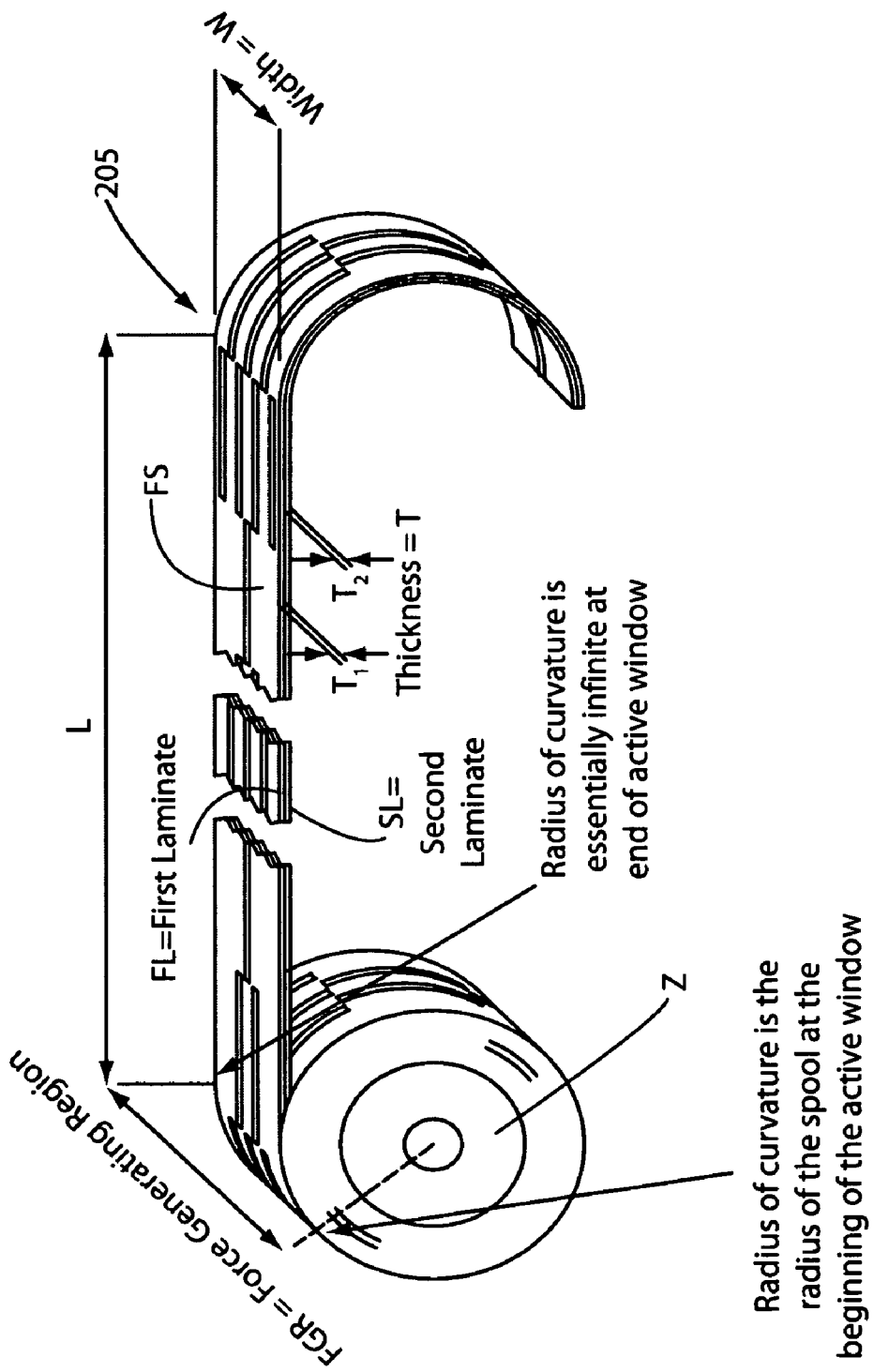
FIG. 28B is a generally perspective view of still another form of variable force spring of a laminate construction that is usable with the apparatus illustrated in FIGS. 25 and 26.

Referring next to FIG. 28 of the drawings, still another form of variable force spring that is usable with the apparatus illustrated in FIGS. 25 and 26 is there shown. In this variable force spring, which is generally designated by the numeral 203, the varying cross-sectional mass along the length of the spring is achieved by a constant force spring wherein the force generating region of the spring has been modified to include a plurality of spaced-apart apertures "AP" along its length. As shown in FIG. 27A, which is a schematic plot (not to scale) of force versus cross-sectional mass, the spring uniquely provides an increasing force in a stair step fashion as it is retracted. It is to be understood, that the apertures formed in the pre-stressed strip of spring material can be located in any desired configuration and can be both transversely and longitudinally spaced-apart to provide the desired force as the spring is retracted.

FIG. 27B is a generally perspective view of yet another form of the retractable spring of a modified configuration that is usable with the apparatus illustrated in FIGS. 25 and 26 is there shown. This latest variable force spring, which is generally designated by the numeral 205, is somewhat similar to that shown in FIG. 27 of the drawings. However, in this latest spring configuration the spring comprises a novel laminate construction made up of a first laminate FL and a second interconnected laminate SL. The varying cross-sectional mass is once again achieved by providing a plurality of the elongated transversely and longitudinally spaced-apart apertures, or slits. However, it is to be understood that, rather than being provided with a plurality of the elongated transversely and longitudinally spaced-apart apertures, or slits, the laminated band portion of the spring can be left without perforations and can be coiled about the spring drum 72 in predetermined varying degrees of tightness to achieve highly specific and desirable linear and non-linear force-distention curves to meet the fluid delivery requirements of the invention.

Having now described the invention in detail in accordance with the requirements of the patent statues, those skilled in this art will have no difficulty in making changes and modifications in the individual parts or their relative assembly in order to meet specific requirements or conditions. Such changes and modifications may be made without departing from the scope and spirit of the invention, as set forth in the following claims.

The invention claimed is:

1. An apparatus for dispensing medicaments to a patient comprising:
  (a) a first assembly including:
    (i) a reservoir housing;
    (ii) an integrally formed, hermetically sealed collapsible container carried by said housing, said collapsible container having a pierceable top wall and a reservoir for containing a medicinal fluid;
    (iii) stored energy means carried by said housing and operably associated with said container for controllably collapsing said container, said stored energy means comprising a plurality of variable force springs, each said variable force spring being movable from a locked extended position to a retracted position; and (iv) spring unlocking means carried by said housing and operably associated with said stored energy means for unlocking said variable force springs from said locked extended position so as to permit said variable force springs to move from said locked extended position to said retracted position;

(b) a second assembly threadably interconnected with said first assembly for movement between a first position and a second position, said second assembly comprising:

(i) a control housing;

(ii) a penetrating member disposed within said control housing for piercing said pierceable top wall of said container upon movement of said second assembly towards said second position and simultaneously with the unlocking of said variable force springs by said spring unlocking means; and (iii) a rate control assembly disposed within said control housing and in communication with said penetrating member for controlling the rate of fluid flow from said container of said first assembly.

2. The apparatus as defined in claim 1 in which said rate control assembly comprises a rate control plate having at least one micro-channel formed therein.

3. The apparatus as defined in claim 1 in which said second assembly includes locking means for preventing relative rotation of said first and second assemblies.

4. The apparatus as defined in claim 1 in which each of said plurality of variable force springs comprises a drum assembly and a band of material wound about said drum assembly, said band of material having a length and exhibiting a cross-sectional mass that varies along said length.

5. The apparatus as defined in claim 1 in which each of said plurality of variable force springs comprises a drum assembly and a band of material wound about said drum assembly, said band of material having a length and a plurality of spaced-apart apertures formed along said length of said band of material.

6. The apparatus as defined in claim 1 in which each of said plurality of variable force springs comprises a drum assembly and a band of material wound about said drum assembly in predetermined varying degrees of tightness.

7. The apparatus as defined in claim 1 in which each of said plurality of variable force springs comprises a drum assembly and in which each of said drum assemblies of each of said variable force springs assemblies comprises:

(a) a spring housing;

(b) a superior spring shaft disposed within said spring housing, said superior spring shaft having an end portion having a locking shoulder, pin internal chamber and a first actuator spring engaging protuberance extending therefrom;

(c) an inferior spring shaft telescopically received within said chamber of said superior spring shaft for movement between a first extended position and a second retracted position, the said inferior spring shaft having a second actuator spring engaging protuberance extending therefrom.

8. The apparatus as defined in claim 7 in which said first assembly includes a main body housing having a plurality of circumferentially spaced locking slots, said locking shoulders of said end portions of said superior spring shafts being received within said locking slots for movement with respect thereto between a first position wherein said locking shoulders are within said locking slots and a second position wherein said locking shoulders are outside of said locking slots.

9. The apparatus as defined in claim 8 in which each of said spring unlocking means of said first assembly comprises a plurality of circumferentially spaced spring actuator assemblies carried by said first assembly, each said spring actuator assembly comprising first and second actuator wings that are pivotally connected to a pivot pin for movement between a retracted position and an expanded position.

10. The apparatus as defined in claim 9 in which each said spring actuator assembly further comprises an actuating pin, said first and second actuator wings of said spring actuator assembly being connected to said actuating pin for movement relative thereto between a first closed position and a second spread position.

11. The apparatus as defined in claim 10 in which, upon said first actuator wings of said spring actuator assemblies moving into said second spread position, said first actuator wings engage said first actuator spring engaging protuberances of said first superior spring shafts so as to move said locking shoulders of said end portions of said superior spring shafts into said second position thereby controllably releasing said variable force springs from said locked extended position to allow said springs to coil about said drum assemblies.

12. An apparatus for dispensing medicaments to a patient comprising:

(a) a first assembly including:

(i) a reservoir housing;

(ii) an integrally formed, hermetically sealed collapsible container carried by said housing, said collapsible container having a pierceable top wall and a reservoir for containing a medicinal fluid;

(iii) stored energy means carried by said housing and operably associated with said container for controllably collapsing said container, said stored energy means comprising a plurality of variable force springs, each said variable force spring being movable from a locked extended position to a retracted position, each of said plurality of variable force springs comprising a drum assembly and a band of material wound about said drum assembly, said band of material having a length and exhibiting a cross-sectional mass that varies along said length; and (iv) spring unlocking means carried by said housing and operably associated with said stored energy means for unlocking said variable force springs from said locked extended position so as to permit said variable force springs to move from said locked extended position to said retracted position, said spring unlocking means comprising a plurality of circumferentially spaced spring actuator assemblies carried by said first assembly, each said spring actuator assembly comprising first and second actuator wings that are pivotally connected to a pivot pin for movement between a retracted position and an expanded position; and (b) a second assembly threadably interconnected with said first assembly for movement between a first position and a second position, said second assembly comprising:

(i) a control housing;

(ii) a penetrating member disposed within said control housing for piercing said pierceable top wall of said container upon movement of said second assembly towards said second position and simultaneously with the unlocking of said variable force springs by said spring unlocking means; and (iii) a rate control assembly disposed within said control housing and in communication with said penetrating member for controlling the rate of fluid flow from said container of said first assembly, said rate control assembly comprises a rate control plate having at least one micro-channel formed therein.

13. The apparatus as defined in claim 12 in which said second assembly includes locking means for preventing relative rotation of said first and second assemblies.

14. The apparatus as defined in claim 12 in which said second assembly further includes an administration set having an inlet in communication with said micro channel of said rate control plate.

15. The apparatus as defined in claim 12 in which said first assembly further includes a carriage disposed within said reservoir housing for supporting said collapsible container, said carriage being operably associated with said stored energy means and being movable thereby between a first retracted position and a second advanced, fluid delivery position.

16. The apparatus as defined in claim 12 in which said first assembly further includes indicator means for indicating the volume of fluid contained within said fluid reservoir of said collapsible container.

17. The apparatus as defined in claim 12 in which each of said plurality of variable force springs comprises a drum assembly and a band of material wound about said drum assembly, said band of material being of a laminate construction.

18. The apparatus as defined in claim 12 in which each said spring actuator assembly further comprises an actuating pin, said first and second actuator wings of said spring actuator assembly being connected to said actuating pin for movement relative thereto between a first closed position and a second spread position.

19. The apparatus as defined in claim 18 in which each of said plurality of variable force springs comprises a drum assembly and in which each of said drum assemblies of each of said variable force springs assemblies comprises:
   (a) a spring housing;
   (b) a superior spring shaft disposed within said spring housing, said superior spring shaft having an end portion having a locking shoulder, pin internal chamber and a first actuator spring engaging protuberance extending there from;
   (c) an inferior spring shaft telescopically received within said chamber of said superior spring shaft for movement between a first extended position and a second retracted position, said the inferior spring shaft having a second actuator spring engaging protuberance extending there from.

20. The apparatus as defined in claim 19 in which said first assembly includes a main body housing having a plurality of circumferentially spaced locking slots, said locking shoulders of said end portions of said superior spring shafts being received within said locking slots for movement with respect thereto between a first position wherein said locking shoulders are within said locking slots and a second position wherein said locking shoulders are outside of said locking slots.

21. The apparatus as defined in claim 20 in which, upon said first actuator wings of said spring actuator assemblies moving into said second spread position, said first actuator wings engage said first actuator spring engaging protuberances of said first superior spring shafts so as to move said locking shoulders of said end portions of said superior spring shafts into said second position thereby controllably releasing said variable force springs from said locked extended position to allow said springs to coil about said drum assemblies.

22. An apparatus for dispensing medicaments to a patient comprising:
   (a) a first assembly including:
      (i) a reservoir housing;
      (ii) a carriage disposed within said reservoir housing for movement between a first retracted position and a second advanced, fluid delivery position;
      (iii) an integrally formed, hermetically sealed collapsible container carried by said carriage, said collapsible container having a pierceable top wall and a reservoir for containing a medicinal fluid;
      (iv) stored energy means carried by said reservoir housing and operably associated with said carriage for moving said carriage between said first retracted position and said second advanced fluid delivery position, said stored energy means comprising a plurality of variable force springs, each said variable force spring being movable from a locked extended position to a retracted position each of said plurality of variable force springs comprising a drum assembly and a band of material wound about said drum assembly each of said drum assemblies comprising:
         a. a spring housing;
         b. a superior spring shaft disposed within said spring housing, said superior spring shaft having an end portion having a locking shoulder, pin internal chamber and a first actuator spring engaging protuberance extending there from;
         c. an inferior spring shaft telescopically received within said chamber of said superior spring shaft for movement between a first extended position and a second retracted position, said the inferior spring shaft having a second actuator spring engaging protuberance extending there from; and
      (v) spring unlocking means carried by said reservoir housing and operably associated with said stored energy means for unlocking said variable force springs from said locked extended position so as to permit said variable force springs to move from said locked extended position to said retracted position said spring unlocking means comprising a plurality of circumferentially spaced spring actuator assemblies carried by said first assembly, each said spring actuator assembly comprising:
         a. an actuating pin;
         b. first and second actuator wings connected to said actuating pin for movement relative thereto between a first closed position and a second spread position; and
   (b) a second assembly threadably interconnected with said first assembly for movement between a first position and a second position, said second assembly comprising:
      (i) a control housing;
      (ii) a penetrating member disposed within said control housing for piercing said pierceable top wall of said container upon movement of said second assembly towards said second position and simultaneously with the unlocking of said variable force springs by said spring unlocking means;
      (iii) a rate control assembly disposed within said control housing and in communication with said penetrating member for controlling the rate of fluid flow from said container of said first assembly, said rate control assembly, comprises a rate control plate having at least one micro-channel formed therein;

(iv) locking means carried by said control housing for preventing relative rotation of said first and second assemblies; and (v) an administration set connected to said control housing, said administration set having an inlet in communication with said micro channel of said rate control plate.

23. The apparatus as defined in claim 22 in which said first assembly further includes indicator means for indicating the volume of fluid contained within said fluid reservoir of said collapsible container.

24. The apparatus as defined in claim 22 in which each of said bands of material of each of said variable force springs is of a laminate construction.

25. The apparatus as defined in claim 22 in which each of said bands of material of each of said variable force springs has a length and exhibits a cross-sectional mass that varies along said length.

26. The apparatus as defined in claim 22 in which each of said bands of material of each of said variable force springs has a length and is provided with a plurality of spaced-apart apertures formed along said length.

27. The apparatus as defined in claim 22 in which each of said bands of material of each of said variable force springs is wound about said drum assembly in predetermined varying degrees of tightness.

* * * * *